(12) United States Patent
Levy et al.

(10) Patent No.: US 8,280,550 B2
(45) Date of Patent: Oct. 2, 2012

(54) CABINET WITH REMOTE INTEGRATION

(75) Inventors: Cynthia Levy, San Jose, CA (US); Richard Caldwell, San Francisco, CA (US); Jennifer Cartright, Loomis, CA (US); Ray Vrabel, San Diego, CA (US); Brad Blackwell, San Francisco, CA (US); John Vahlberg, Mountain View, CA (US)

(73) Assignee: Omnicell, Inc., Mountain View, CA (US)

(*) Notice: Subject to any disclaimer, the term of this patent is extended or adjusted under 35 U.S.C. 154(b) by 395 days.

(21) Appl. No.: 12/502,172

(22) Filed: Jul. 13, 2009

(65) Prior Publication Data

US 2010/0042437 A1 Feb. 18, 2010

Related U.S. Application Data

(63) Continuation-in-part of application No. 12/140,964, filed on Jun. 17, 2008, now Pat. No. 8,126,590.

(51) Int. Cl.
    *G06F 17/00* (2006.01)
(52) U.S. Cl. ......... 700/241; 700/236; 700/240; 700/244
(58) Field of Classification Search .................. 700/236, 700/237, 240, 241, 244
    See application file for complete search history.

(56) References Cited

U.S. PATENT DOCUMENTS

| | | | |
|---|---|---|---|
| 4,518,208 A | 5/1985 | Marder | |
| 4,847,764 A * | 7/1989 | Halvorson | ................ 700/231 |
| 5,139,321 A | 8/1992 | Beardsley | |
| 5,190,185 A | 3/1993 | Blechl | |
| 5,208,762 A | 5/1993 | Charhut et al. | |
| 5,377,864 A | 1/1995 | Blechl et al. | |
| 5,468,118 A | 11/1995 | LePoire | |
| 5,745,366 A | 4/1998 | Higham et al. | |
| 5,805,455 A | 9/1998 | Lipps | |
| 5,805,456 A | 9/1998 | Higham et al. | |
| 5,905,653 A * | 5/1999 | Higham et al. | ............... 700/244 |
| 5,927,540 A | 7/1999 | Godlewski | |
| 6,011,999 A | 1/2000 | Holmes | |
| 6,039,467 A | 3/2000 | Holmes | |
| 6,068,156 A | 5/2000 | Liff et al. | |

(Continued)

FOREIGN PATENT DOCUMENTS

WO  WO 02/03230  1/2002

(Continued)

OTHER PUBLICATIONS

U.S. Appl. No. 12/140,964, filed Jun. 17, 2008, Office Action mailed Jan. 5, 2011, 12 pages.

(Continued)

*Primary Examiner* — Timothy Waggoner
(74) *Attorney, Agent, or Firm* — Kilpatrick Townsend & Stockton LLP

(57) ABSTRACT

Devices, systems, and methods are described for remotely managing items that are configured to be stored in at least one dispensing device. This includes receiving user identification information at a host computer system from an electronic device that is remotely located from the dispensing device. This also includes transmitting from the host computer system to the electronic device a disposition of at least one item, wherein the at least one item is associated with a patient. Further, this includes receiving, at the host computer system from the remote electronic device, information about the item originating from the dispensing device, wherein the information includes a further disposition of the item.

30 Claims, 17 Drawing Sheets

U.S. PATENT DOCUMENTS

| | | | |
|---|---|---|---|
| 6,112,502 A * | 9/2000 | Frederick et al. | 700/237 |
| 6,151,536 A | 11/2000 | Arnold et al. | |
| 6,163,737 A | 12/2000 | Fedor et al. | |
| 6,170,929 B1 | 1/2001 | Wilson et al. | |
| 6,219,587 B1 * | 4/2001 | Ahlin et al. | 700/233 |
| 6,272,394 B1 | 8/2001 | Lipps | |
| 6,354,783 B1 | 3/2002 | Stoy et al. | |
| 6,385,505 B1 | 5/2002 | Lipps | |
| 6,435,370 B1 | 8/2002 | Wilson | |
| 6,564,121 B1 | 5/2003 | Wallace et al. | |
| 6,604,019 B2 | 8/2003 | Ahlin et al. | |
| 6,609,047 B1 | 8/2003 | Lipps | |
| 6,611,733 B1 | 8/2003 | De La Huerga | |
| 6,636,780 B1 * | 10/2003 | Haitin et al. | 700/236 |
| 6,640,159 B2 | 10/2003 | Holmes et al. | |
| 6,735,497 B2 * | 5/2004 | Wallace et al. | 700/231 |
| 6,760,643 B2 | 7/2004 | Lipps | |
| 6,775,591 B1 | 8/2004 | Shoenfeld | |
| 6,847,861 B2 | 1/2005 | Lunak et al. | |
| 6,975,922 B2 | 12/2005 | Duncan et al. | |
| 7,006,893 B2 | 2/2006 | Hart et al. | |
| 7,010,389 B2 | 3/2006 | Lunak et al. | |
| 7,080,755 B2 | 7/2006 | Handfield et al. | |
| 7,100,792 B2 | 9/2006 | Hunter et al. | |
| 7,119,689 B2 | 10/2006 | Mallett et al. | |
| 7,155,306 B2 | 12/2006 | Haitin et al. | |
| 7,249,688 B2 | 7/2007 | Hunter et al. | |
| 7,348,884 B2 | 3/2008 | Higham | |
| 7,395,945 B2 | 7/2008 | Godlewski | |
| 7,571,024 B2 | 8/2009 | Duncan et al. | |
| 7,588,167 B2 | 9/2009 | Hunter et al. | |
| 7,654,261 B1 | 2/2010 | Rockhold | |
| 7,675,421 B2 | 3/2010 | Higham | |
| 7,728,711 B2 | 6/2010 | Shoenfeld | |
| 7,835,819 B2 | 11/2010 | Duncan et al. | |
| 2001/0032035 A1 | 10/2001 | Holmes et al. | |
| 2002/0130065 A1 | 9/2002 | Bloom | |
| 2003/0055531 A1 | 3/2003 | Liff et al. | |
| 2003/0074218 A1 | 4/2003 | Liff et al. | |
| 2003/0088333 A1 | 5/2003 | Liff et al. | |
| 2003/0093295 A1 | 5/2003 | Lilly et al. | |
| 2003/0120384 A1 | 6/2003 | Haitin et al. | |
| 2004/0148055 A1 | 7/2004 | Shoenfeld | |
| 2004/0176985 A1 | 9/2004 | Lilly et al. | |
| 2006/0224736 A1 | 10/2006 | Graziado et al. | |
| 2006/0229551 A1 | 10/2006 | Martinez et al. | |
| 2007/0038330 A1 | 2/2007 | Sullivan | |
| 2007/0088461 A1 * | 4/2007 | Haitin et al. | 700/241 |
| 2008/0319575 A1 | 12/2008 | Vahlberg et al. | |
| 2008/0319576 A1 | 12/2008 | Vahlberg et al. | |
| 2008/0319577 A1 | 12/2008 | Vahlberg et al. | |
| 2008/0319578 A1 | 12/2008 | Vahlberg et al. | |
| 2008/0319579 A1 | 12/2008 | Vahlberg et al. | |
| 2008/0319580 A1 | 12/2008 | Vahlberg et al. | |
| 2008/0319581 A1 | 12/2008 | Vahlberg et al. | |
| 2008/0319789 A1 | 12/2008 | Vahlberg et al. | |
| 2008/0319790 A1 | 12/2008 | Vahlberg et al. | |

FOREIGN PATENT DOCUMENTS

| | | |
|---|---|---|
| WO | WO 03/081378 A2 | 10/2003 |
| WO | WO 03/105057 A1 | 12/2003 |
| WO | WO 2007/035185 A2 | 3/2007 |

OTHER PUBLICATIONS

U.S. Appl. No. 12/140,970, filed Jun. 17, 2008, Office Action mailed Feb. 16, 2011, 10 pages.

U.S. Appl. No. 12/140,966, filed Jun. 17, 2008, Office Action mailed Mar. 7, 2011, 6 pages.

Search Report and Written Opinion for Singapore Patent Application No. 200908458-3, mailed Jan. 21, 2011, 20 pages.

U.S. Appl. No. 12/140,969, filed Jun. 14, 2008, Final Office Action mailed Mar. 14, 2011, 14 pages.

U.S. Appl. No. 12/140,971, filed Jun. 17, 2008, Office Action mailed Apr. 8, 2011, 6 pages.

European Search Report for Application No. EP 08771396, mailed May 12, 2011, 11 pages.

U.S. Appl. No. 12/140,964, filed Jun. 17, 2008, Final Office Action mailed Jun. 20, 2011, 12 pages.

U.S. Appl. No. 12/140,966, filed Jun. 17, 2008, Final Office Action mailed Aug. 15, 2011, 7 pages.

U.S. Appl. No. 12/140,970, filed Jun. 17, 2008, Final Office Action mailed Aug. 3, 2011, 11 pages.

U.S. Appl. No. 12/140,975, filed Jun. 17, 2008, Office Action mailed May 2, 2011, 6 pages.

U.S. Appl. No. 12/140,979, filed Jun. 14, 2008, Office Action mailed May 16, 2011, 5 pages.

U.S. Appl. No. 12/140,985, filed Jun. 17, 2008, Office Action mailed Jun. 23, 2011, 6 pages.

PCT International Search Report and Written Opinion mailed Sep. 7, 2010; International Application No. PCT/US2010/041834, 10 pages.

McKesson: Empowering Healthcare, "McKesson's Connect-RN Integrates IT and Automation to Ensure Patient Safety and Enhance Nursing Efficiency", Newsroom Release (Business Wire), Mar. 22, 2007, 1 page.

McKesson Connect-RN, "Empower Nurses to Optimize Medication Administration", 2005, 2 pages.

U.S. Appl. No. 12/140,969, filed Jun. 14, 2008, Office Action mailed Sep. 14, 2010, 12 pages.

International Search Report and Written Opinion dated Dec. 8, 2008, corresponding to International Application No. PCT/US08/67386, filed Jun. 18, 2008, 17 pages.

* cited by examiner

| Omnicell - Anywhere RN - Windows Internet Explorer | | | | | | | | □ □ × |
|---|---|---|---|---|---|---|---|---|
| Omnicell Anywhere RN™ | | | | | | | | Options▼ Log Out |

Pending Cabinet Requests

| Pending Issues | Pending Returns | | | | | | |
|---|---|---|---|---|---|---|---|
| Medications to Return | | | | | | | |
| — Green, Ronald | ID: 0032765 | Room: 302B | PSB Location: 4N med room | | | | |
| Medication | Issued | Administered | Returned | Wasted | Undoc | Return Qty | |
| — Alendronate 10 mg TAB (Fosamax) | 40 MG | 10 MG | 10 MG | 0 | 10 MG | − 1 + TAB | Cancel |
| Issued: 05/02/08 07:00 | | Stevens, Norma 40 MG | | | | | |
| Administered: 05/02/08 09:10 | | Stevens, Norma 40 MG | | | | | |
| Citalopram 20mg TAB (Celexa) | 40 MG | 0 | 0 | 0 | 40 MG | − 2 + EA | Cancel |
| — Logan, Janice | ID: 0032788 | Room: 304A | PSB Location: 4N med room | | | | |
| Medication | Issued | Administered | Returned | Wasted | Undoc | Return Qty | |
| Alendronate 10 mg TAB (Fosamax) | 30 MG | 10 MG | 0 | 0 | 20 MG | − 2 + TAB | Cancel |
| Citalopram 20mg TAB (Celexa) | 20 MG | 0 | 0 | 0 | 20 MG | − 1 + EA | Cancel |
| Newell, Howard | ID: 0032799 | Room: 307A | PSB Location: 4N med room | | | | |

Save Changes  Cancel All  Close

User: Omnitech 10  Site/Area: OC - AREA  May 1, 2008  13:21

Fig. 12b

CABINET WITH REMOTE INTEGRATION

CROSS-REFERENCES TO RELATED APPLICATIONS

This Application is a non-provisional application and a continuation-in-part of U.S. patent application Ser. No. 12/140,964, filed on Jun. 17, 2008 now U.S. Pat. No. 8,126, 590, entitled "Patient-Specific Bin Systems, Methods, and Devices." This Application hereby incorporates by reference herein the content of the aforementioned application in its entirety and for all purposes.

BACKGROUND OF THE INVENTION

The present invention relates in general to the remote managing, documenting distribution, and monitoring of items from a storage system. In particular, the present invention relates to remote managing, distribution, documenting of distribution, and monitoring of items used in a healthcare environment. In many cases, this involves the distribution, issuing, return, and wasting of medications, pharmaceuticals, and medical supplies to and from dispensing units.

Many industries require items to be available for use at specific locations. For example, in hospitals, practitioners may find it convenient to place medications and medical supply items near where patients are being treated. A nursing station is one such location, as nurses may find it more efficient to have certain medications and supplies readily available. The items being dispensed may need to be documented. This documentation requirement may be due to law, regulation, or likelihood of theft. For these and other reasons, the dispensing device may be required to be locked. Depending on the type of items dispensed, the environment where the items are used, and other variables, a variety of dispensing units and cabinets have been employed.

Typically, documentation or information may be entered directly to a dispensing device before medications, supplies, or other items may be removed by an authorized user. The entering of such information may be time consuming, inconvenient, and may cause a backlog of users waiting to access the dispensing device. It would therefore be beneficial to create systems, methods or devices that address these issues and that minimize the amount of direct interaction with the dispensing units.

BRIEF SUMMARY OF THE INVENTION

The invention provides various systems, methods, and devices that facilitate the storage and distribution of medications and supply items, including an accounting for how such items are used. In many cases, efficiencies are increased by providing the caregiver with various access points so that the required documentation may be entered at convenient locations and times, rather than directly at dispensing units or devices employed to hold such items. In some cases, the dispensing devices (e.g., cabinets, drawers, and shelves) may include a number of bins for storing the items, and some of the bins may be allocated as patient-specific bins available to be assigned for patient-specific storage and dispensing functions. Rather than requiring the healthcare worker to directly interface with such dispensing devices each time that an item needs to be removed, returned, wasted or otherwise accounted for, the caregiver may remotely provide appropriate information at various access points. These access points may include laptops, terminals, bedside devices, mobile devices, or a device which can display a webpage. The access point may be accessible via a private network, such as a secured hospital network, or a public network, such as the Internet.

For example, in some embodiments of the invention, a method is provided for remotely managing items that are configured to be stored in at least one dispensing device. User identification information, such as login information, may be sent from an electronic device that is remotely located from a dispensing device. A user at the remote device may request a disposition of at least one item originating from one of dispensing devices. Information regarding the item may be received at the electronic device remotely located from the dispensing device. This information or disposition may relate to a wasting of the item, the return of the item to a dispensing device, or to some other disposition of the item. The user may transmit information regarding the previously removed item from the remote electronic device. In this way, the caregiver may remotely provide a request to return an item at a later time or to waste an item remotely, and remotely provide follow up information on the request.

The items a caregiver might be managing remotely may be controlled medical substances, including pharmaceuticals, and medical supplies. Further, the caregiver may not be returning or wasting entire items. Rather, a portion of the item may have been used, with a further disposition being necessary for only a remaining portion of the item.

In some embodiments of the invention, a system for dispensing items is provided. The system may include one or more dispensing devices, such as cabinets. These dispensing devices may be configured to hold one or more items. The dispensing device may be able to accept user input via a processor. The system may also include a host system. This host system is configured to communicate with the dispensing device. User identification information may be input to an electronic device. The electronic device may be remotely located from the dispensing device. A user request, such as by a caregiver, for a disposition of an item originating from the dispensing device may be made at the remote electronic device. In this way, the caregiver may remotely provide a request to return or waste an item from a remote location. Information regarding the further disposition of the item may be sent to the remote electronic device. The caregiver or user may then document and transmit further information about the disposition of the item from the remote electronic device.

In another exemplary embodiment of the invention, a method of monitoring the distribution of items is present. The method includes a subset of data contained in a first patient record being retrieved from an administration records system. A second patient record that contains fields for information regarding medication of a patient may be created on a host system. At least some of the data contained in the first patient record may be incorporated into the second patient record. Some or all of the second patient record may be transmitted to an electronic device. The electronic device may be remotely located from a dispensing device. This second patient record may be modified at the remote electronic device. Such a modification may include a disposition of a controlled medical substance, medical supply, or other item stored in the dispensing device. In this way, a caregiver or other user may be saved from having to create a patient record for a patient that has an existing patient record in an administration records system. The caregiver may then be able to document information relating to the returning or wasting of the controlled medical substances, medications, or items related to the patient.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a second label that distinguishes among the similar components. If only the first reference label is used in the specification, the description is applicable to any one of the similar components having the same first reference label irrespective of the second reference label.

FIG. 7 illustrates an embodiment of a wastes and returns window.

FIG. 12 illustrates an embodiment of a return window.

FIG. 12b illustrates an embodiment of a pending returns window.

DETAILED DESCRIPTION OF THE INVENTION

Figure 1:
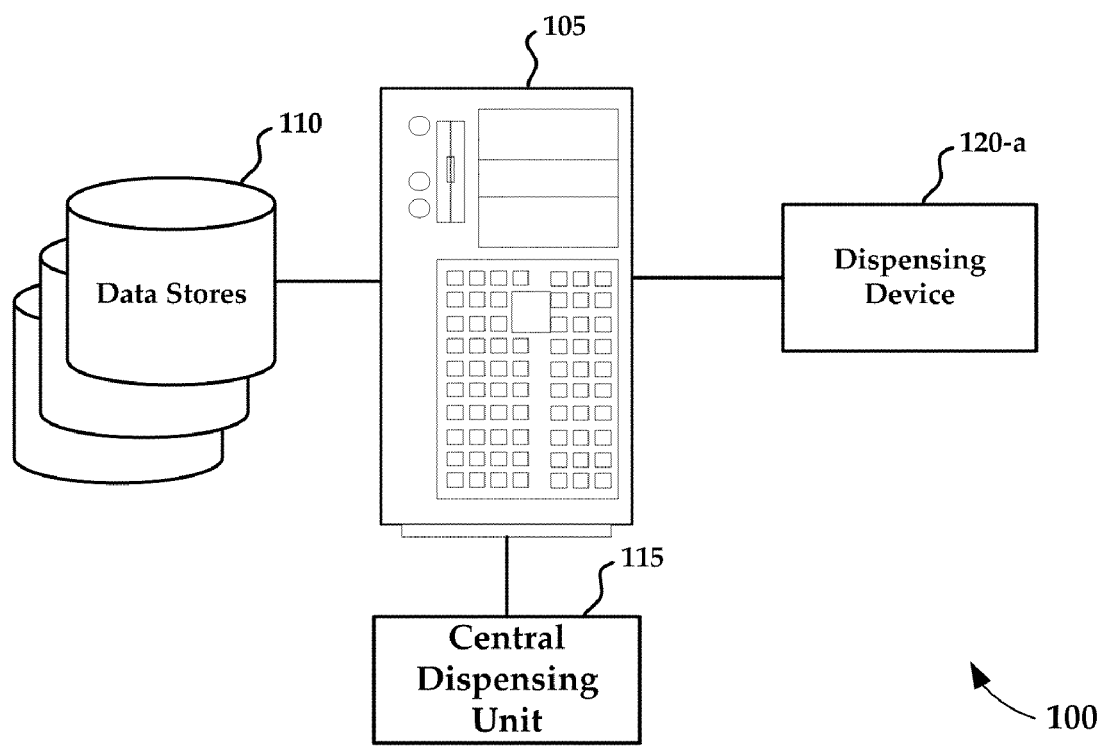
FIG. 1 illustrates an embodiment of a dispensing system with remote integration.

The invention provides various ways to dispense items and account for such items in an efficient manner. The invention may be used in connection with a wide variety of dispensing devices employed to store and dispense such items. Such dispensing devices may be constructed from a cabinet having various storage locations for storing the items. Dispensing devices may include cabinets, drawers, bins, shelves, or any combination thereof. These dispensing devices may be freely accessible or may be secured with various locks. Such is often the case when storing pharmaceuticals, controlled medical supplies, and other controlled items.

It may be necessary for the location and disposition of items to be monitored, recorded, or documented. Such requirements may be necessary to comply with the law, a hospital's policies, or for safety. While the location of these items may need to be constantly monitored, users, such as nurses, doctors, or other medical professionals, may require frequent access to the items. For example, a user may need to remove an item from the dispensing device several times per day, such as to administer the item to a patient following each meal. In some cases, only a portion of an item may be administered to a patient. The administered amount may need to be documented, and the remaining portion of the item returned to a dispensing device. As another example, a user may initially remove an item from a dispensing device then later determine the item should not have been removed. In such cases, the user may need to return the entire item to a dispensing device and document its return.

Accordingly, a variety of situations arise where items may need to be removed from a dispensing device, discarded, destroyed, or returned to a dispensing device. The person responsible for the item may be required to provide information to document the action required. The required information may involve: a reason for the issuing/removing, returning, discarding, or destroying the item, the identity of a witness to the returning, discarding, or destroying of the item, patient information, time and date information, or any other related information. While such information may be documented via a dispensing device, this may lead to problems. For example, if a user is documenting her actions involving stored items at a dispensing device, it may delay another user from documenting her actions. Also, it may prevent another user from issuing/removing an item from the dispensing device. In some embodiments, the invention provides for documenting and information gathering at a device remote from the dispensing device. The dispensing device or a host computer system may communicate with the remote device, such as a computer terminal, handheld electronic device, laptop computer, or a similar device. This may allow a user to provide some or all of the necessary information for documentation of the use of an item away from the dispensing device.

Remote documenting and information gathering may decrease the amount of information a user must supply at the dispensing device, or eliminate the need to physically visit a dispensing device. A common procedure involving controlled medical substances may be referred to as "wasting." "Wasting" may mean the physical destruction of an item or a portion of an item, or the discarding of an item or a portion of an item. Documenting the discarding or physical destruction of an item or a portion of an item remote from a dispensing device may allow a user to completely avoid visiting a dispensing device. This may present a significant savings in time, effort, and efficiency. These benefits may be especially apparent if the dispensing device is located on a different floor and/or in a different building.

While a user or agent of the user may need to physically visit a dispensing device to return an item or a portion of an item, documenting the return of the item remotely may still present significant time savings for the user and other users. Documenting a return remotely may be more comfortable, such as at a desk or home as opposed to at a dispensing device, and more time-efficient, especially if other users are waiting to access the dispensing device. Documenting a return remotely may allow a user to provide the majority of necessary information remotely, with minimal information provided at the dispensing device, such as only the user's username and password.

Further, documenting a return to a dispensing device or the wasting of an item or a portion of an item may not require a bedside administration system. A bedside administration system may require that documentation be performed before, during, or after a medication is administered to a patient or before, during, or after a supply is used. For example, when a medication is given to a patient, a barcode associated with the medication and a barcode associated with the patient may need to be scanned. Similar systems include electronic administration documentation or electronic medication administrations records. Such systems are used to document the dose, the date, the time, and the patient when a medicine is administered. As long as a remote device, such as a computer, can occasionally remotely communicate with the server or other device serving as a host for the dispensing system, no further dependency on any other system may be present. A remote device that interacts with a remote integration system may allow for wasting to be documented at a location where the item or portion of then item is desired to be wasted.

Despite not requiring a bedside administration system, a dispensing system with remote integration may have the capability interact with various bedside administration systems, produced by various manufacturers. For example, a dispensing system with remote integration may interact with SAFETYMED sold by OMNICELL, among other bedside administration systems offered by other manufacturers. The incorporation of a bedside administration system may create an additional layer of accountability for the location and use of supplies and medicines. Further, the integration of such a bedside administration system may simplify and expedite the entry of information into the remote integration system. By way of example only, if a nurse has removed 500 mg of Drug A from a dispensing cabinet, the use of a bedside administration system for the administering of 300 mg of Drug A to the patient would result in the dispensing system with remote integration being notified that only 200 mg of Drug A is left unaccounted for. The 300 mg of Drug A would be automatically denoted as administered to the patient in the remote integration system. In addition to automatically denoting the amount administered to a patient, other values may be automatically entered into the remote integration system. Such values may include: if and how much waste is outstanding, if and how much of a return is outstanding, and the amount that must be returned or wasted.

Referring to FIG. 1, an example of a dispensing system with remote integration 100 is illustrated. Such a system may be used for storing, managing, and distributing items. These items may include medications, pharmaceuticals, medical supplies, controlled medical substances, controlled medical supplies (such as syringes), and the like (hereinafter collectively referred to as "items"). Alternatively, these items may be any objects that are desired to be stored, managed, or distributed in a controlled manner. The use of these items may need to be documented and/or witnessed. The system 100 includes a dispensing device 120-*a* (e.g. cabinet with a number of storage locations, such as shelves, drawers, or bins) for dispensing items. The system also includes a server computer system 105, which is communicatively connected with data stores 110, a central dispensing unit 115, and the dispensing device 120-*a*. In some embodiments, one or more of these components may be removed or substituted with other devices.

A dispensing device may be any device for dispensing items, such as a cabinet for storing medications for patients in a healthcare facility. In other embodiments, aspects of the system may be used in different settings to dispense a range of varying objects. A dispensing device may be stationary, such as a nursing cabinet serving a particular area of a hospital, or may be mobile, such as a cart with drawers. Examples of several successful dispensing cabinets are described in U.S. Pat. Nos. 6,760,643; 6,609,047; 6,272,394; 6,385,505; 5,805,455; 5,805,456; 5,745,366; 5,905,653; 5,927,540; 6,039,467; 6,151,536; 5,377,864; and 5,190,185, the complete disclosures of which are herein incorporated by reference. The dispensing device 120-*a* may be in wired or wireless communication with the central server computer system 105.

The dispensing device 120-*a* may be located at a nursing station serving a number of rooms, in an operating room, in an emergency room, in an intensive care unit, or in a number of other locations within or outside the medical field, as evident to those skilled in the art. The dispensing device may be profiled by patient, with certain patients having a certain area or areas within the dispensing device assigned to them. In some embodiments, the dispensing device is stocked with specific items or medications. In such embodiments, a request for a particular item or medication may be issued from the dispensing device no matter who the patient is. The dispensing device 120-*a* may be mobile. The dispensing device 120-*a* may include a computer and console configured to manage the storage and distribution of items at the dispensing device, and networked to communicate continuously or occasionally with the server computer system 105. There may be different levels of security for particular sections or bins within the dispensing device 120-*a*. Sections of the dispensing device 120-*a* may be locked while other sections are not locked.

Items to be stocked at the dispensing device 120-*a* may be stored at a central dispensing unit 115. The central dispensing unit 115 may be a cabinet, dispensing device, warehouse, pharmacy, or any other place where items to stock a dispensing device 120-*a* may be stored. The central dispensing unit 115 may be in communication with the central server computer system 105. Such communication allows for the tracking of the stocking of the dispensing unit 120-*a*.

The dispensing device 120-*a* may be in communication with a central server computer system 105. Data related to the patients, contents and access to the dispensing device may be stored at the central server computer. In some embodiments, the data may be stored at the dispensing device 120-*a*. The central server computer system 105 may communicate with a number of data stores 110. The data stores 110 may be local to the central server computer system 105 or may be located remotely. The data stores 110 may store information on patients, contents of the dispensing devices, users who have access to the dispensing devices, or any other pertinent information to the operation of the system 100. In some embodiments, several dispensing devices 120 may be present, with each connected to the central server computer system 105. In some embodiments, the functionality of a central server computer system 105, and data stores 110 may be integrated with the dispensing device 120-*a* or dispensing devices 120.

Figure 2:
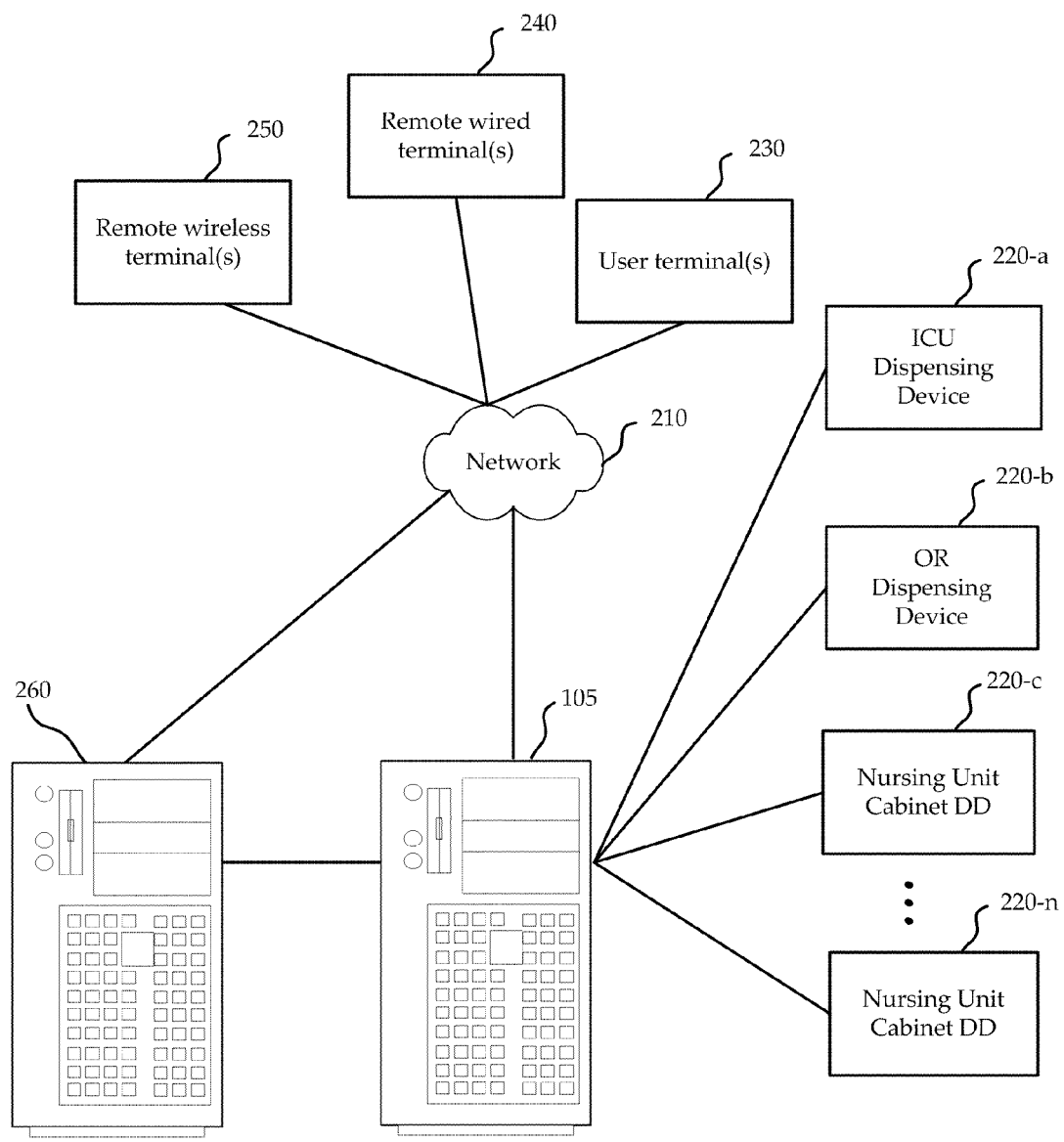
FIG. 2 illustrates another embodiment of a dispensing system with remote integration.

Referring to FIG. 2, a simplified block diagram of an embodiment of a dispensing system with remote integration 200 is illustrated. The system 200 of FIG. 2 may illustrate an alternative embodiment of the system 100 described with reference to FIG. 1. The system 200 may include some of the same components as the system 100 of FIG. 1, such as the central server computer system 105.

The system 200 of FIG. 2 includes a central server computer system 105, which is communicatively connected to each of the dispensing devices 220. The central server computer system 105 of FIG. 2 may perform any of the functions previously described with reference to the central server computer system 105 of FIG. 1. The central server computer system 105 may be communicatively connected through a network 210 to a remote wireless terminal 250, a remote wired terminal 240, and/or a user terminal 230. The central server computer system 105 may be connected to any number of terminals. These terminals may be local or remote from the central server computer system 105 and the dispensing devices.

The remote wireless terminal 250 may be a computer, a workstation, a laptop, a mobile device, a hand-held electronic device, or any other device capable of wirelessly communicating with the central server computer system 105. The remote wireless terminal 250 may be any device capable of displaying a webpage. The remote wireless terminal 250 may interface with a network 210, through a wireless router. The remote wired terminal 240 may also be a workstation, a laptop, a kiosk or any other device capable of communicating with the central server computer system 105. The remote wired terminal 240 may be any device capable of displaying a web page. The remote wired terminal 240 may have a physical connection to the network 210, such as via a local area network cable. The ability of the remote wired terminal 240 and the remote wireless terminal 250 to interact with the central server computer system 105 may be similar, or may include different functionality. The remote wireless terminal 250 and the remote wired terminal 240 may be physically separated from the dispensing devices 220. Alternatively, the remote wireless terminal 250 and the remote wired terminal 240 may be located adjacent to a dispensing device 220.

The user terminal 230 may be remote from the dispensing devices 220 or may be local to the dispensing devices 220. In some embodiments, a user terminal 230 may be a computer integrated with the dispensing devices 220. The user terminal 230 may be any device capable of communicating with the network 210, or the central server computer system 105, and displaying a webpage.

Functionality available at the dispensing devices 220 may be available at the terminals 230, 240, and 250. This functionality may include the ability to document the use of items. For example, if an authorized user wishes to remove an item from a dispensing device 220, he may be required to identify himself, the patient, the name of the item, the amount of the item, the prescribing doctor, the time administered to the patient, and/or any other information relevant to the removal (alternatively referred to as issuance) of the item. The information required to be entered by the user or available to the user may vary depending on the industry, the law governing the location of the dispensing device, or the regulations of the entity operating the dispensing device. The necessary information may be input at the dispensing devices 220. The terminals 230, 240, and 250 may allow at least some of this information to be input remotely from the dispensing cabinets.

Four typical operations involving a dispensing device 220 are issuance of an item, issue of an item, return of at least some of an item, and wasting at least some of an item stored at or removed from a dispensing device 220 or other depository. A user may request an item be issued from a dispensing device 220. When a user requests an item be issued from a dispensing device, the user may need to acquire authorization from a doctor, practitioner, or other authorized user. This authorization may happen through the central server computer system 105, orally, or in a written form. In some embodiments, the user may be required to obtain authorization from a pharmacy before issuance of an item from a dispensing device 220.

In some embodiments, the user will require authorization from a doctor, practitioner, or other authorized user and a pharmacy or other agency maintaining control over the items. In an emergency situation, the user, depending on her authorization to the dispensing device 220 and the central server computer system 105, may be able to override any authorization or documentation requirements. Such an override may allow items to be dispensed from the dispensing device 220 without authorization. In some embodiments, the user may be required to enter the necessary information after the emergency situation has subsided. For example, at a healthcare facility, a nurse may determine a certain prescription medicine is immediately necessary to save a patient's life, with no time available for approval from a pharmacy or doctor. The nurse may be able to override the authorization requirements of the dispensing device 220 and access the item necessary. The nurse may then enter pertinent information at the dispensing device, a wireless terminal, a wired terminal, or user terminal at a later time.

A request for issuing of an item may be made from any terminal 230, 240, 250 that can communicate with the central server computer system 105. This may be in place of, independent of, or integrated with any bedside administration product as previously described, and allow a user to remotely request an item prior to the user physically going to a dispensing device. Depending on the user's access level, the item requested, the hospital's policy, and local law, varying requirements may be set as to the reporting requirements the user must provide for issuing of the item from the dispensing device 220.

Further, while the removal or issuing of items from a dispensing device is often discussed as from a dispensing device, items may also be issued from other locations. For example, an item may be issued to a user by a pharmacy, a central dispensing location, or some other depository. The item being initially issued by a depository other than a dispensing device may not impact the use of a dispensing system with remote integration. For example, if an item is directly issued from a pharmacy to a user, the item may still be documented and wasted using a dispensing system with remote integration, or if a return is necessary, the item may be documented and returned to a dispensing device or to some other depository. In some embodiments involving returns, the location or device the item is initially issued from has no bearing on the location or device the item is returned to.

Figure 3:
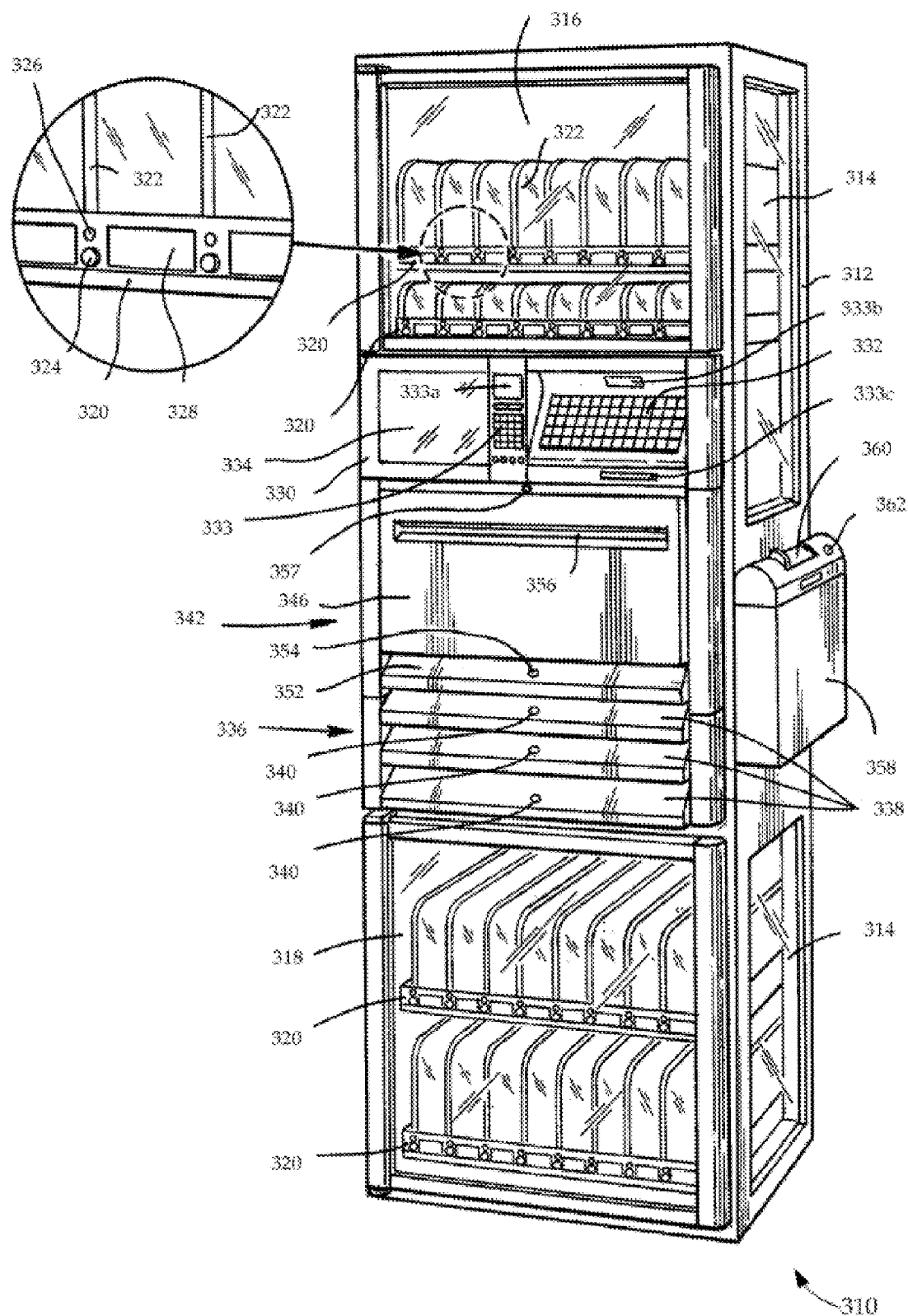
FIG. 3 illustrates an embodiment of a dispensing device.

FIG. 3 illustrates an embodiment of a dispensing device 310. The patient dispensing device in this embodiment is a cabinet 310, which may be constructed from a cabinet frame 312 with various transparent panels 314. Cabinet 310 further includes a pair of doors 316 and 318 that enclose a series of shelves 320 within the cabinet 310. These enclosed areas may be temperature-controlled or refrigerated in various embodiments. Shelves 320 may be divided into various storage locations using adjustable dividers 322. Further, associated with each storage location may be an item button 324 that may be pressed to record the issuance or removal of items from or placement of items into each storage location. A light 326 may also be positioned adjacent each item button to guide the user to a specific storage location. Further, a label 328 may be associated with each storage location and may include information on the items stored in a particular storage location. Optionally, doors 316 and 318 may be locked and only opened when appropriate identification information has been entered into a computer 330 or at a remote terminal, device, or computer. Hence, to remove an item from one of the shelves 320, a user may enter appropriate identification information directly into computer 330, with associated information possibly entered via a remote device or computer. In other embodiments, the storage locations or zones could vary in size, configuration, and security. The locations may be allocated for assignment to patients as patient specific bins (PSBs), and the locations available may be adjusted depending on current and projected use levels and occupancy factors. PSB allocation and patient bin assignment may be made by the computer 330, or received from a remote location (e.g., central server computer system 105 of FIG. 1A). The locations may also be allocated by item size, type, classification, security level, need for refrigeration, alphabetically, or any other organization scheme.

To facilitate the entry of information, the computer 330 may include a traditional keyboard 332 and a key pad 333 containing numeric keys. A touch pad 333a may be disposed above key pad 333 and used to control a pointer on a display screen 334. Disposed below key pad 333 are keys to control the contrast of display screen 334 and to control the sound that may be emitted from a speaker 333b. Disposed below keyboard 332 is a receipt port 333c through which printed receipts or labels may pass. The panel containing keyboard 332 may be rotated downward to gain access to the receipt printer. The illustrated computer configuration is for purposes of example only; in other embodiments, any subset of the features may be employed, and particular implementations and input devices may vary.

One use of the various input devices on the computer 330 is to permit the user to select one or more items that are to be removed. If information is entered by the user at a remote terminal, device, or computer, the amount of information that must be entered at the computer 330 may be reduced. A list of items, generated by the computer 330 or received from the central server computer system 105, may be displayed on the display screen 334. Further, display screen 334 may be a touch screen display that permits various items to be selected simply by touching them on a display screen 334. Computer 330 may be coupled to any type of computer network to permit various information to be supplied to computer 330 (e.g., by the central server computer system 105 of FIG. 1A). For example, stock or restock lists may be transmitted from the central server computer system 105, as may lists for cleaning or other removal of items.

When the appropriate items have been selected, doors 316 and 318 may be unlocked (in cases where doors 316 and 318 are already locked) and the appropriate lights 326 may be lighted to guide the user to the items selected. Upon issuance or removal of the items, the user may press item buttons 324 a number of times corresponding to the number of items removed. A similar process may be used for restocking items into the storage locations.

A cabinet 310 may further include a pharmacy section 336 with various drawers 338 for holding pharmaceutical items or other types of items that need additional security. When appropriate information has been entered into computer 330, the appropriate drawers 338 may be unlocked and lights 340 on the drawers lighted to guide the user to the appropriate doors. Drawers 338 may conveniently include various bins, shelves, or storage locations that may be assigned to different items, categories of items, or patients, which may optionally have lockable lids to provide additional security to the items. The lids corresponding to bins that have the selected items may be unlocked and users may be guided to the unlocked bins using lights in a manner similar to that described with shelves 320.

In one embodiment, pharmacy section 336 further includes a dispensing unit area 342. Briefly, dispensing unit area 342 includes a dispensing unit frame that is insertable into cabinet frame 312 of cabinet 310. Coupled to the dispensing unit frame is a door 346 that may be opened to provide access to dispenser frame. Although dispensing mechanisms may typically be associated with items for use by a number of patients, particular bins associated with dispensing mechanisms may be assigned to patients in some embodiments. Below dispenser frame is a dispense drawer 352 that receives items that fall from dispensing mechanisms after such items have been selected at computer 330. Bins within the dispense drawer 352 may be assigned as PSBs on a temporary or more permanent basis to specific patients. The dispense drawer 352 may include a light 354 to guide the user to the dispense drawer 352 during dispensing operations. A handle 356 may be provided on door 346 to facilitate opening of door 346. The door 346 may include a light 357 to guide the user to the door 346 during dispensing operations.

In some cases, dispensed items may need to be returned to cabinet 310. In some situations, various laws, regulations, or facility policies prohibit dispensed items from being placed back into cabinet 310. As such, attached to (or otherwise integrated into) cabinet 310 may be a return unit 358 having a slidable (or rotatable) door 360 that may be opened to permit the item to be placed into the return unit 358. When returning the item, information regarding the return may be entered into computer 330. A light 362 on the return unit 358 may be lighted to indicate to the user that the item may be returned. The return unit 358 is preferably configured so that once an item is placed into the unit, the item cannot be retrieved from the return unit 358 unless a restock user or technician is authorized to gain access. For example, a restock technician may be required to enter appropriate information into computer 330 to cause the return unit 358 to unlock to allow access to the items within.

Although one specific arrangement of cabinet 310 has been described, it will be appreciated that any subset or combination of the above components may be used with a variety of dispensing cabinets. For example, a dispensing mechanism and unit may be placed within a cabinet that is used solely for dispensing pharmaceuticals and may only include drawers similar to drawers 338. As another alternative, such mechanisms and units may be placed in a cabinet that only includes shelves that are similar to shelves 320. Further, such mechanisms and units may be used in cabinets having multiple shelves and/or drawers that are placed side-by-side in a vertical arrangement. Also, a dispensing cabinet may include multiple dispensing unit areas 342. These may be sized to the same size, or may be different sizes. Still further, in some cases such dispensing cabinets may include other types of shelves, racks, drawers, and the like to facilitate the storage of items.

Figure 4:
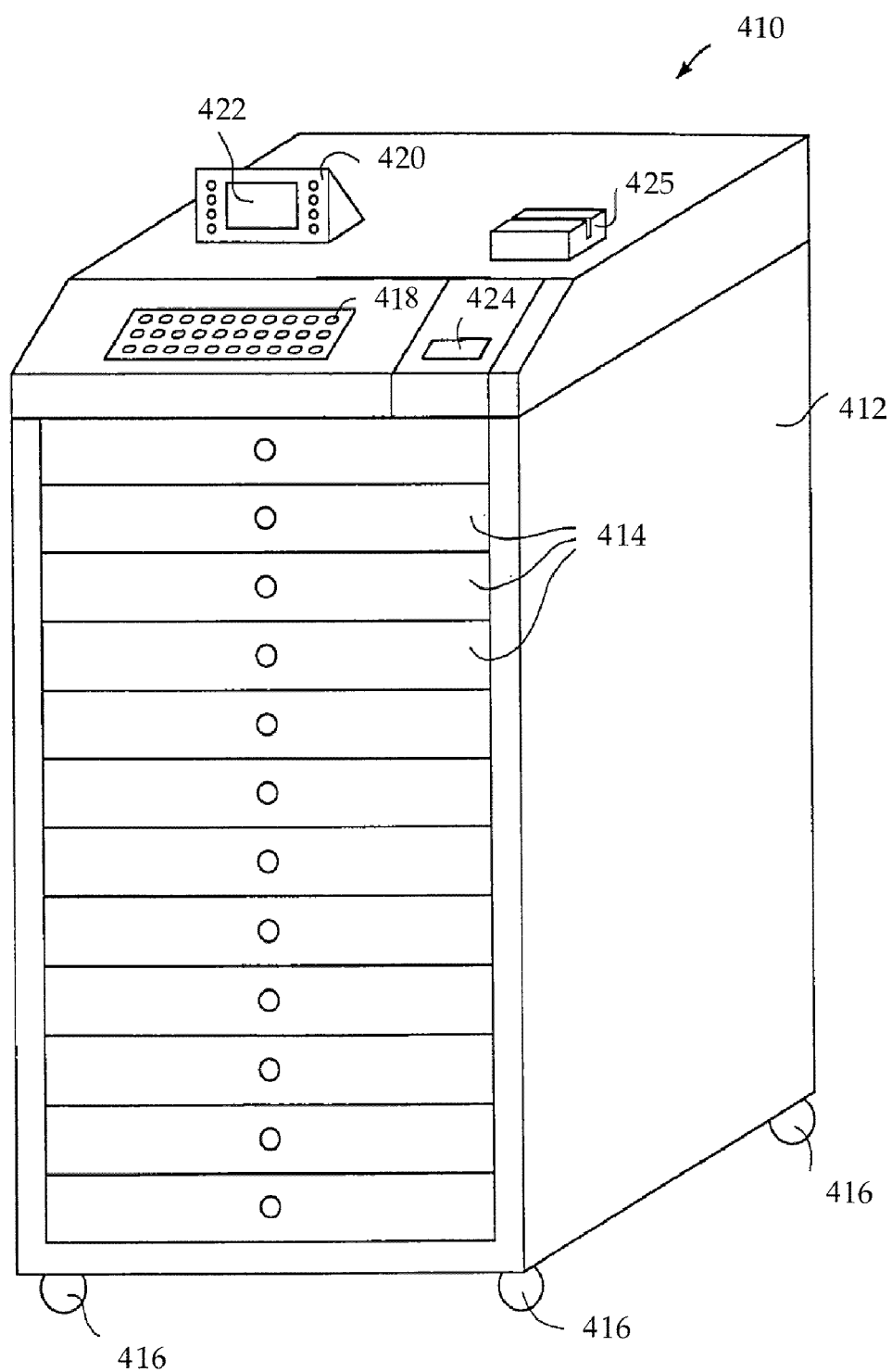
FIG. 4 illustrates another embodiment of a dispensing device.

There are a number of different configurations of other types of dispensing devices 120 and 220 of FIGS. 1 and 2, respectively. FIG. 4 illustrates yet another example of such a device. The illustrated dispensing device 410 may include one or all of the functions of the patient dispensing devices 120 described with reference to the system 100 of FIG. 1. Thus, the device 410 may be in wired or wireless communication with the central server computer system 105.

The dispensing device 410 includes a cabinet 412 having a number of retractable drawers 414. Although shown with 12 drawers, the number of drawers may be varied. The cabinet 412 may rest upon wheels 416, which allow the dispensing device 410 to be wheeled throughout the healthcare facility. The cabinet may be battery powered and configured to communicate wirelessly (e.g., to allow communication while in transit). The cabinet 412 may be fashioned with various dimensions.

The dispensing device 410 further includes an integrated computer (hidden within cabinet 412) and a keyboard 418 for entering various information into the computer. For example, keyboard 418 may be employed to enter patient identification information, user identification information, requests for item stocking, issuing, and removal, and the like into the computer. Optionally, the dispensing device 410 may further include a second entry device 420 which is connected to the computer and includes a screen 422 which allows the user to scroll through various lists of information in order to select a highlighted item. For example, a caregiver may scroll through a list of patient names or item names in order to select a certain patient or to enter an item removal, issuance, or stocking request. In one embodiment, the screen may be a color touch screen. The touch screen may be configured to allow a user to interact with the dispensing cabinet, with or without having to use the keyboard, mouse, or other traditional methods, as the touch screen functionality allows a user to touch their selection directly. The touch screen may be a color touch screen, and color distinctions may inform and guide the user (e.g., alerts or warnings in yellow, item unavailability in grey, next steps in green).

A printer 424 may be provided on cabinet 412 to print various reports or labels generated by the computer. In other embodiments, some of the computing functionality for a device 410 (e.g., display, input device, reader, etc.) may be detachable or otherwise separate from the device 410, and may communicate wirelessly with the device 410 or central server computer system 105.

The cabinet 412 may further include a magnetic, bar code, RFID, data collector or other reader 425 which is connected (directly or wirelessly) to the computer. Such a reader 425 may be employed on any of the dispensing devices 120 described herein. It may be configured to manually or automatically scan for types and associated quantities or levels then provide the data to the cabinet 512 or to the central computer system 105. The reader 425 may be provided to allow a user, a patient, or particular medications or other supplies to be identified. For example, an identifier (e.g., magnetic, bar code, RFID, or other identifier) may be read from a medication container when an item is stocked, restocked, or removed. The identifier (and amount) may then be transmitted to the central server computer system 105 or otherwise stored, for purposes of tracking inventory. Similarly, an identifier (e.g., magnetic, bar code, RFID, or other identifier from an access card or other instrument) may be read from the user of the device or patient associated with the device. The reader 425 may also be employed to read an identification device associated with the drawers, as well.

To retrieve or remove items of a particular patient, a user (e.g., a nurse user or other caregiver, patient, automated system, etc.) may enter user identification (e.g., a password, PIN, smart card, RFID, combination thereof, etc.) using keyboard 418, reader 425, or entry device 420. The user (or the computer 330) may then identify the patient. The patient identification may be entered by the user using keyboard 418, reader 425, or entry device 420. The user may select the desired medication or other supplies, or the computer (or a central server computer system 105) may direct the user (via lights or a listing, for example). The user may also enter the number of items of the selected type that are to be removed or retrieved for the patient. The user may then retract the proper drawer and will be led to the correct bin. There may also be a step of verifying the count of specific items taken, by prompting the user to enter via keyboard 418 or entry device 420 the number of items of the specific type that were removed or supplied and the number remaining. A record of this event may also be maintained within the computer, or may be transmitted to the central server computer system 105 of FIG. 1, or elsewhere. A variety of other removal alternatives may be used, as well.

For stocking and restocking of items into dispensing device 410, the pharmacy or other central dispensing unit (e.g., central dispensing unit 115 of FIG. 1) may prepare all items for a particular cart fill at a particular PSB or set of PSBs together in a set of packages or other container. The cart may also be stocked with various items not segregated by patient. For example, certain locations in the cart may always contain certain items, or the items in the cart may be varied based on present or future need. If the use of PSBs are desired, all of the medications for a given PSB may be gathered and consolidated at the pharmacy or other central dispensing unit before they are placed in the cart. The computer for the cabinet 410, or perhaps the central server computer system 105 of FIG. 1, may transmit the restock list to the pharmacy, or a list may be processed locally at the pharmacy. The process of gathering and consolidating the supplies for a particular PSB may therefore take place at the pharmacy or other central dispensing unit, instead of at the dispensing device 410. This may provide a more secure environment, and result in less loss. It may also be more efficient for a pharmacist instead of a nurse user to perform these tasks.

To stock or restock a cart with items, the user may enter user, patient, and/or packages/container identification (e.g., a password, PIN, label, serial number, bar code, identification device, smart card, RFID, etc.) using keyboard 418, reader 425, or entry device 420. Thus, the entry of user, patient, or packages/container identification information (or any combination thereof) may trigger the restocking process. The computer for the cabinet 410 (perhaps controlled by the central server computer system 105 of FIG. 1), may direct the user (e.g., via lights or screen information) to place the packages/container in the appropriate locations or PSBs. The action may be logged, and perhaps transmitted to the central server computer system 105.

In other embodiments, instead of having the pharmacy or other dispensing entity consolidate the restocking items, individual items may be placed on a shelf, drawer, storage location, or a PSB on an item-by-item basis at the dispensing device 410. For example, the pharmacy or other central dispensing unit (e.g., central dispensing unit 115 of FIG. 1), or central server computer system 105 of FIG. 1, may be in frequent contact with dispensing devices. Information may be exchanged with the dispensing devices, and in particular information on the current quantity on hand for each item in each dispensing device. At regular intervals (e.g., every morning) a restock list may be generated for each dispensing device, detailing the total quantity of each item to be taken to the dispensing devices to bring the quantity in each drawer, storage location, shelve, or PSB up to a predetermined (or dynamically calculated) par level.

As another alternative, a pre-stocked liner for one or more bins, shelves, drawers, or storage locations may be prepared at the pharmacy, central dispensing unit, or elsewhere. The replacement liner may be configured to have the same arrangement of bins and items or a different arrangement of bins and items. A variety of other restocking systems may be used, as well. Although the retrieval and stocking are described with reference to the cabinet 410 of FIG. 4, these procedures may be applied to other dispensing devices (e.g., the dispensing device 120 of FIG. 1), as well. The stocking or restocking may be performed when a patient first checks into a hospital, when there is a need for refills, or in managing a transfer, to name a few instances.

Figure 4B:
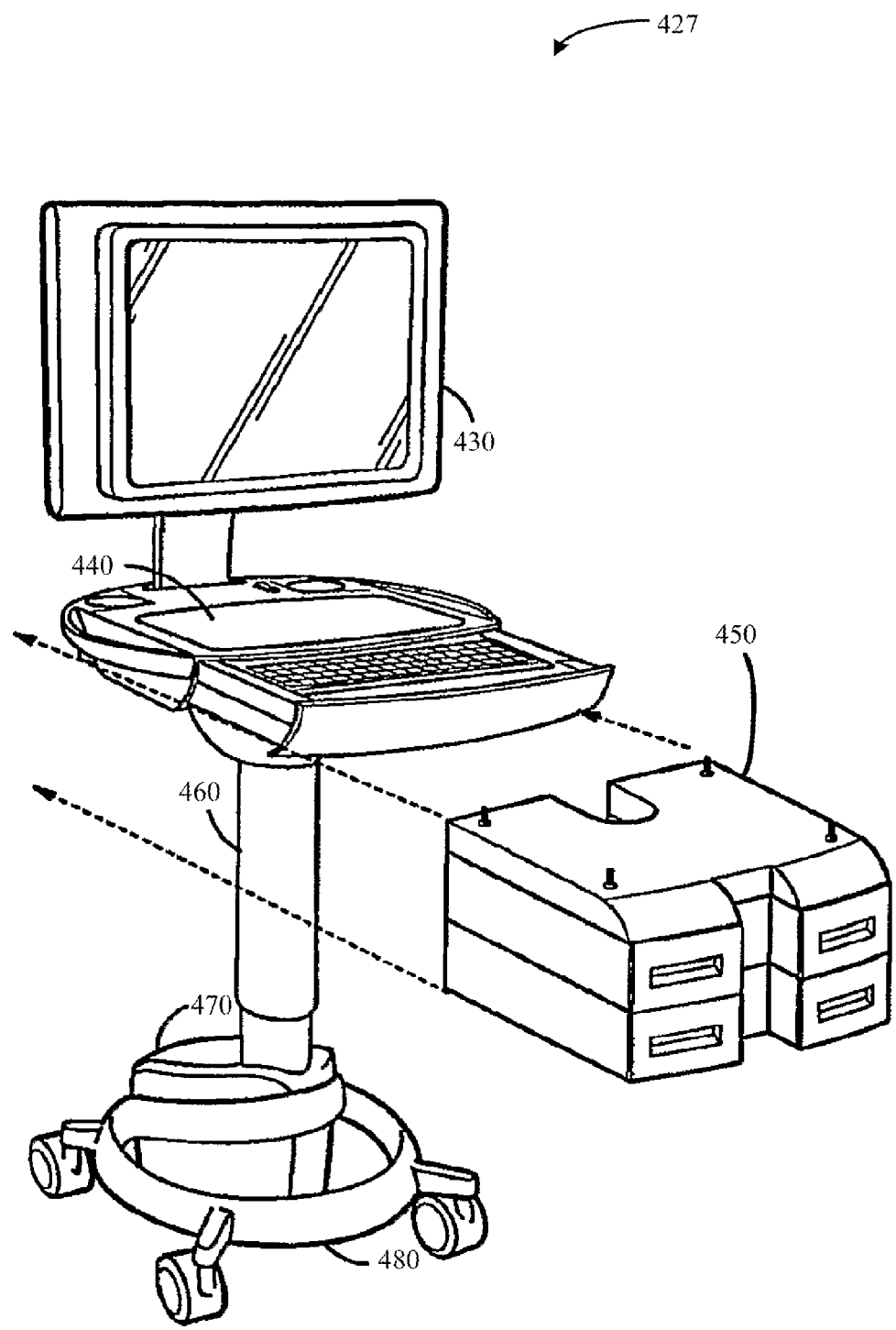
FIG. 4B illustrates another embodiment of a dispensing device.

FIG. 4B illustrates an embodiment of a cart 427 that may be used in conjunction with a dispensing system with remote integration. Such a cart 427 may be a RIO cart manufactured by OMNICELL, or it may be some other cart. The cart 427 of FIG. 4B is an example only, other carts with different drawer or bin configurations may be used. The cart 427 may have a number of drawers 450 attached to a mast 460. These drawers 450 may be controlled by a drawer controller. A drawer controller may lock or unlock each of the drawers 450. In some embodiments, no drawers 450 are present. A battery 470 may be attached to the cart 427 to provide power. The mast 460 may be mounted to a rolling base 480. A rolling base 480 may allow the cart to be wheeled between patients, rooms, and dispensing devices. The cart 427 may also include a work surface 440. Such a surface may be used for writing, preparation of medicines or supplies, storage, or any other item or activity. The cart 427 may also have guiding lights (not pictured). Such guiding lights may indicate the location of items associated with a particular patient and/or may indicate the location of a particular medicine or item. The guiding lights may be useful to visibly indicate to a user where an item is located, or where a return should be placed.

The computer/monitor 430 may be a terminal capable of connecting to a network, either wirelessly or via a cable. Such a terminal may allow for communication with the central server computer system and interaction with the dispensing system with remote integration. The computer/monitor 430 may serve as any other terminal capable of interacting with a dispensing system. The drawers 450 may be specific to particular drugs or particular patients. A user or nurse may have the ability, through the dispensing system with remote integration, to retrieve a list of medicines, supplies, or patients that he or she needs or will be responsible for. This listing may be automatically generated by the dispensing system with remote integration. Alternatively, the user may create a listing of his or her patients via the dispensing system with remote integration. The dispensing system with remote integration may then produce a listing of medicines or supplies that the user must load from a dispensing device, a pharmacy, or some other centralized location to the cart 427. This may include an automatic assignment process where a patient is assigned a particular drawer on the cart 427 by the dispensing system with remote integration. The generation of the listing for stocking the cart 427 may automatically grant the user access to a dispensing device. The stocking process may result in the user being granted access to some or all of the drawers 450 of the cart. The dispensing system with remote integration may transmit to the cart 427 a listing of patients, medicines, or supplies that the cart 427 or the user is associated with. The user may then be able to remove medicines or supplies from the cart to administer to a patient, to waste, or to return to a dispensing cabinet or other storage center. The transmission of instructions to the cart 427 may be done with alternatively configured mobile carts. In some embodiments, a patient is assigned one drawer on the cart 427. In other embodiments, multiple patients may be assigned to a drawer, or one patient may be assigned with multiple drawers.

Figure 5:
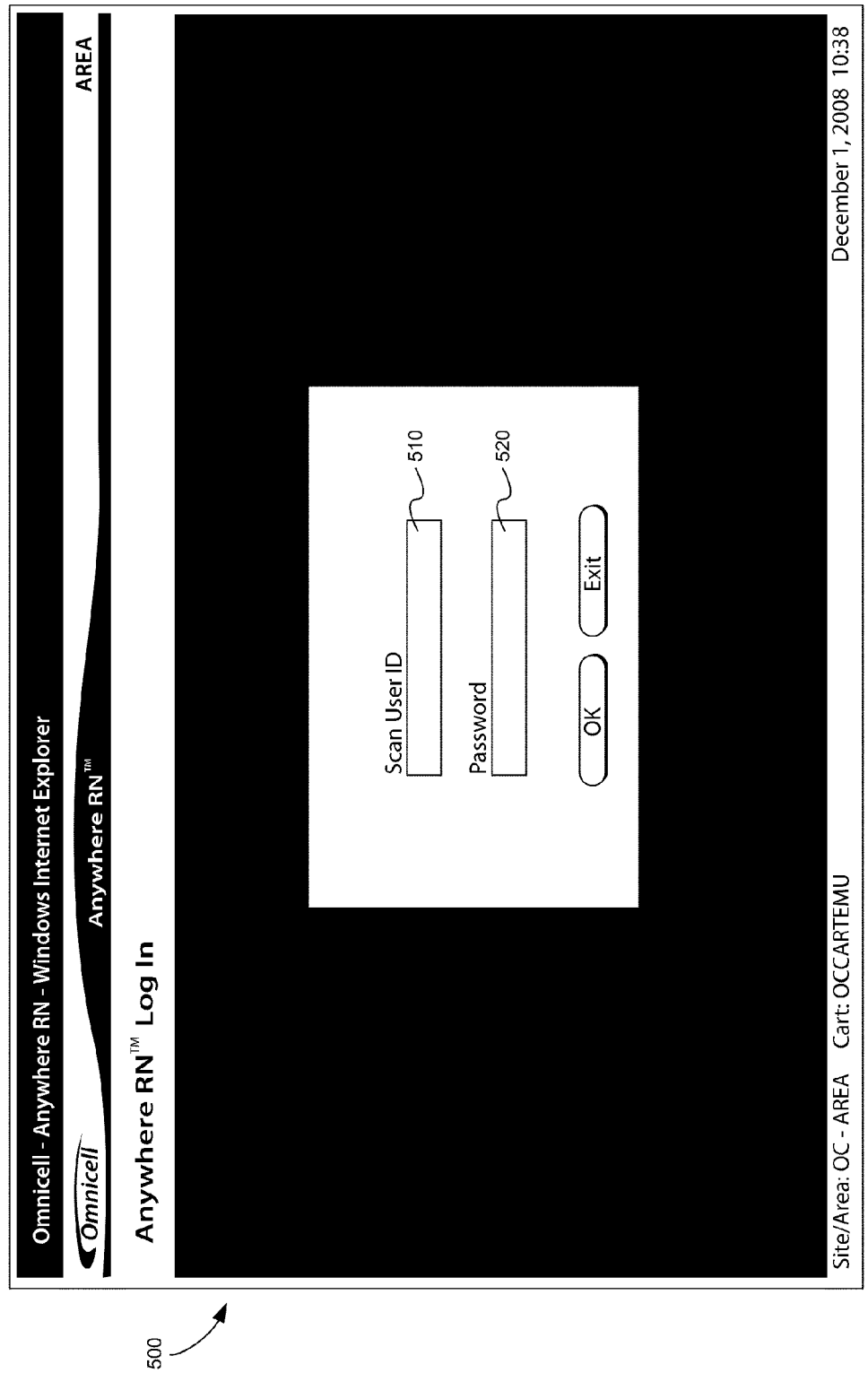
FIG. 5 illustrates an embodiment of a login window.

At a terminal 230, 240 or 250 a user may be required to log in and provide a password or other identifier to verify her identity. FIG. 5 illustrates an embodiment of a login window 500 for a remote terminal such as 230, 240, or 250 of FIG. 2. A user may be required to enter a user identification 510. The identification number may be a number, a username or screen-name. A user may also be required to enter a password 520. In some embodiments, the user identification 510 and the password 520 are replaced with a biometric device, such as a fingerprint scanner or a retina scanner, capable of identifying and verifying the identity of the user. Further, in some embodiments, a user identification 510 may be input from a identification card with a magnetic stripe or from a barcode. Verification of the user's identity then may be completed using a password or a form of biometric identification.

The central computer server system 105 may communicate with, either directly or through the network 210, an administration records computer server system 260. This allows information to either automatically or manually be imported from administration records to the records used for managing items related to patients. For example, information such as a patient's name, room number, a patient identification, allergies, and prescriptions may be copied from the administration records computer server system 260 so that the information does not need to be manually entered to the central server computer system 105. In some embodiments, the administration records computer server system 260 is incorporated with the central server computer system 105.

Interaction of the central computer server system 105 and an administration records computer server system 260, such as a bedside administration system, may provide additional benefits. As previously described, information stored at the administration records computer server system 260 may be used by the dispensing system with remote integration 200 to determine how much waste is outstanding, if any returns are outstanding, the amount of an item that will need to be wasted, and the amount of an item that will need to be returned to the dispensing device. Such information may be used to automatically fill fields to the expected value of wastes and returns in windows requiring values from the user. Further, integration between the dispensing system with remote integration 200 and the administration records computer server system 260 may allow for automated report generation of items or medications that have been removed or issued from a dispensing device, but have not been administered, wasted, or returned to a dispensing device. Such a report may be on a patient by patient basis or may be based on the responsible user or medical professional.

The user identification 510 and the password 520 may be verified at a terminal, a dispensing unit, or at the central server computer system. Proper identification of a user, such as providing a valid user identification 510 and a password 520 may result in accessing being granted to an interface for interacting with the dispensing units.

Figure 6:
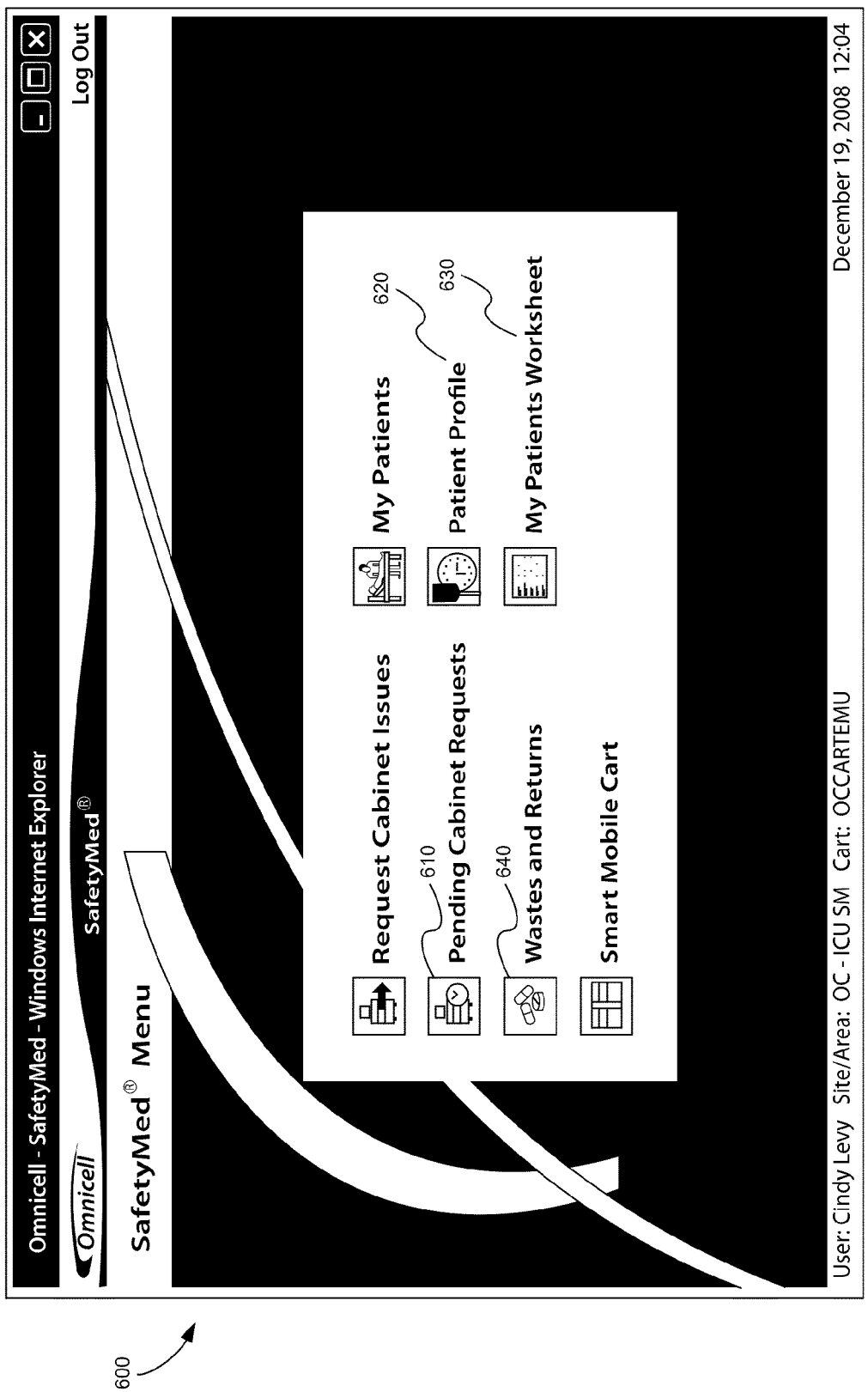
FIG. 6 illustrates an embodiment of a menu window.

Once access has been granted, the user may be presented with a menu, such as menu 600 of FIG. 6. The menu screen may contain various menu options, including: "Pending Cabinet Requests" 610, "Patient Profile" 620, "My Patients Worksheet" 630, and "Wastes and Returns" 640. The "Pending Cabinet Requests" 610 option may display a screen to allow the user to remotely generate a list of medications and their quantities to issue from a dispensing device. The "Patient Profile" 620 option may allow a user to select, scan, or otherwise identify a patient the user wants to work with. This option may display information, including medication information, related to a specific patient. The "My Patients" worksheet 630 option may provide an overview of the user's patients. This overview may include information such as which items are due to be administered to a patient.

The menu screen 600 may include a menu item such as "Wastes and Returns" 640. In some embodiments, selecting "Wastes and Returns" 640 results in a display of a window of information and options relating to the wasting and return of items to a dispensing device. "Wasting" may mean the physical destruction of the item or the portion of the item, or the discarding of the item or the portion of the item. Returning an item refers to an item than has been removed from a dispensing device or other depository, and is to be placed back in the same dispensing device or a different dispensing device. This may refer to the entire item or a portion of the item.

Figure 7:
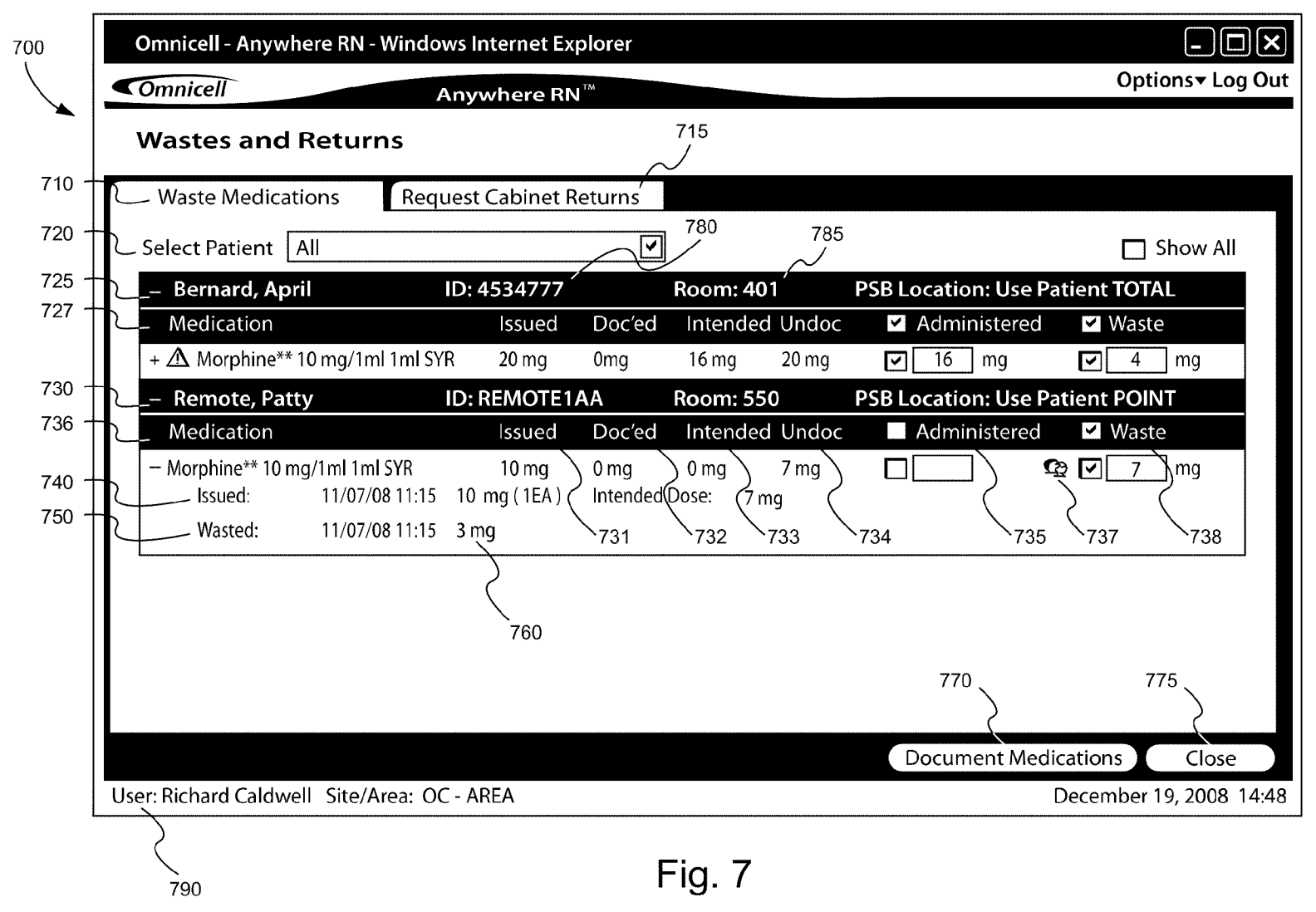

FIG. 7 illustrates an embodiment of what a menu selection, such as "Waste and Returns" 640 of FIG. 6 may look like. Such a display may be provided on a remote terminal, such as those described in relation to FIG. 4. Selecting "Waste and Returns" 640 of FIG. 6 may display the waste and returns screen 700 of FIG. 7, or it may display a different waste and returns screen. Likewise, the waste and returns screen 700 may be associated with the menu option waste and returns 640 of FIG. 6 or may be associated with a different menu option on a different menu. The waste and return screen 700 may be divided into separate sections entitled in separate "Waste Medications" 710 and "Request Cabinet Returns"

715 sections, such as with tabs. In some embodiments, these sections are provided in one screen.

In the embodiment of FIG. 7, the waste medications 710 tab is active. Therefore, information pertinent to the wasting of items is displayed. In the embodiment shown, medications requiring wasting by the user are shown. In some embodiments, all patients, or all patients related to the user may be displayed, regardless of whether wasting of a medication or item related to the patient is required. In the waste and returns screen 700, a patient's name 730 is displayed. Associated with this patient, are the following category headings: Medication 736, Issued 731, Doc'ed 732, Intended 733, Undoc 734, Administered 735, and Waste 736. As those with skill in the art will recognize, the categories of data maintained may vary substantially based on the industry or field of use the items are being used in.

Entering wasting information via a waste medications screen from a remote device may allow a user to complete a wasting of an item remotely. This may decrease the number of visits the user needs to make to a dispensing unit. This may be especially useful if the dispensing unit is located a significant distance from where the user wishes to complete the wasting of the item. For example, in a hospital complex, the user may wish to complete the wasting in a different building than the location of the dispensing device. If a wasting requires a witness, this may save at least two people from traveling to the dispensing device. If all necessary information for a wasting is documented via a remote device, such as through an interface similar to the waste and returns screen 700, a return visit to the dispensing device may have been eliminated.

Medication 736 may list the medication or item associated with the patient 730 that is to be wasted. In this instance, the medication 736 is morphine. The medication 736 heading may refer to the brand name or the generic name of a medication. Alternate names may be displayed in parenthesis, or otherwise set off from the primary name of the medication.

The issued 731 heading may represent the amount and/or strength of an item or medication issued to the patient 730. The quantity and unit of issue may be displayed. A separate heading also titled "issued" may be present. This field may provide additional information related to issue, such as the date and time issued. The "Doc'ed" 732 header may list the amount of the medication 736 administered to the patient 730, minus the amount of canceled administrations. The "Intended" 733 heading may list the amount of the medication 736 specified as the intended dose when the medication 736 was issued. This amount may clear when an amount of the medication 736 is wasted. The "Undoc" 734 heading may list the amount of the medication 736 that has not yet been documented.

The "Administered" 735 heading may allow a user to check (and uncheck) a box, and enter a numerical amount. In some embodiments, the user may be given a list of values to select from. When the box is unchecked, the user may be prevented from entered an amount administered. After entering an amount under the administered 735 heading, the user may select the "Document Medications" button 770 to save and update the display with the new information. Selecting "Close" 775 may also save and update the waste medications 710 and may return the user to a menu, such as menu screen 600 of FIG. 6.

The "Waste" 738 heading may allow a user to check (and uncheck) a box, and enter a numerical amount. In some embodiments, the user may be given a list of values to select from. If a witness is required for the wasting process, an icon 737 or other indication may alert the user that a witness is necessary for the wasting procedure. Selecting the icon 737 may provide the user or witness with additional information, options, or a separate menu. When the box is unchecked, the user may be prevented from entered an amount to waste. After providing an amount under the "Waste" 738 heading, the user may select the "Document Medications" button 770 to save and update the display with the new information. Selecting "Close" 775 may also save and update the waste medications 710 and may return the user to a menu, such as menu screen 600 of FIG. 6. A separate heading, entitled "Wasted" 750 may be displayed showing the time, date, and amount 760 wasted.

For some medications, such as those that are non-multiuse medications, the amount to be wasted under the "Waste" heading 738 may be automatically filled in. The user may or may not be able to edit this default amount. Depending on the amount entered by the user, the other amounts may be automatically adjusted such that the documented and wasted amounts sum to the total undocumented amount. In some embodiments, the user is allowed to specify any amount, with no determination of whether the amounts sum to the "Issued" or "Undoc'd" amounts.

In addition to the patients' names 725 and 730, additional information may be displayed. A patient's identification number 780 and/or room number 785 may be displayed. If a patient has no active or future order for an item or medication displayed, an icon 727 or other alert may display to alert the user that the patient has no active orders for the medication 736. If the user clicks on the icon 727, additional information may be displayed. A "Select Patient" 720 heading with an associated menu, may allow the user to filter the list of patients. For example, the user may be able to display all patients associated with the user, a specific patient, or all patients that have pending medications or items to be wasted. Additionally, the user and site/area may be displayed. A display of the name of the user or the username currently logged in and/or the site/area (such as "Emergency Room") may prevent a user from wasting or returning medication or items while logged to another user's account.

When a user selects an option related to waste, such as "Waste" 738, "Document Medications" 770, or "Close" 775, a pop-up window, or other display may appear requiring witness information. If a witness icon 737 is present, such a display may also appear.

Figure 8:
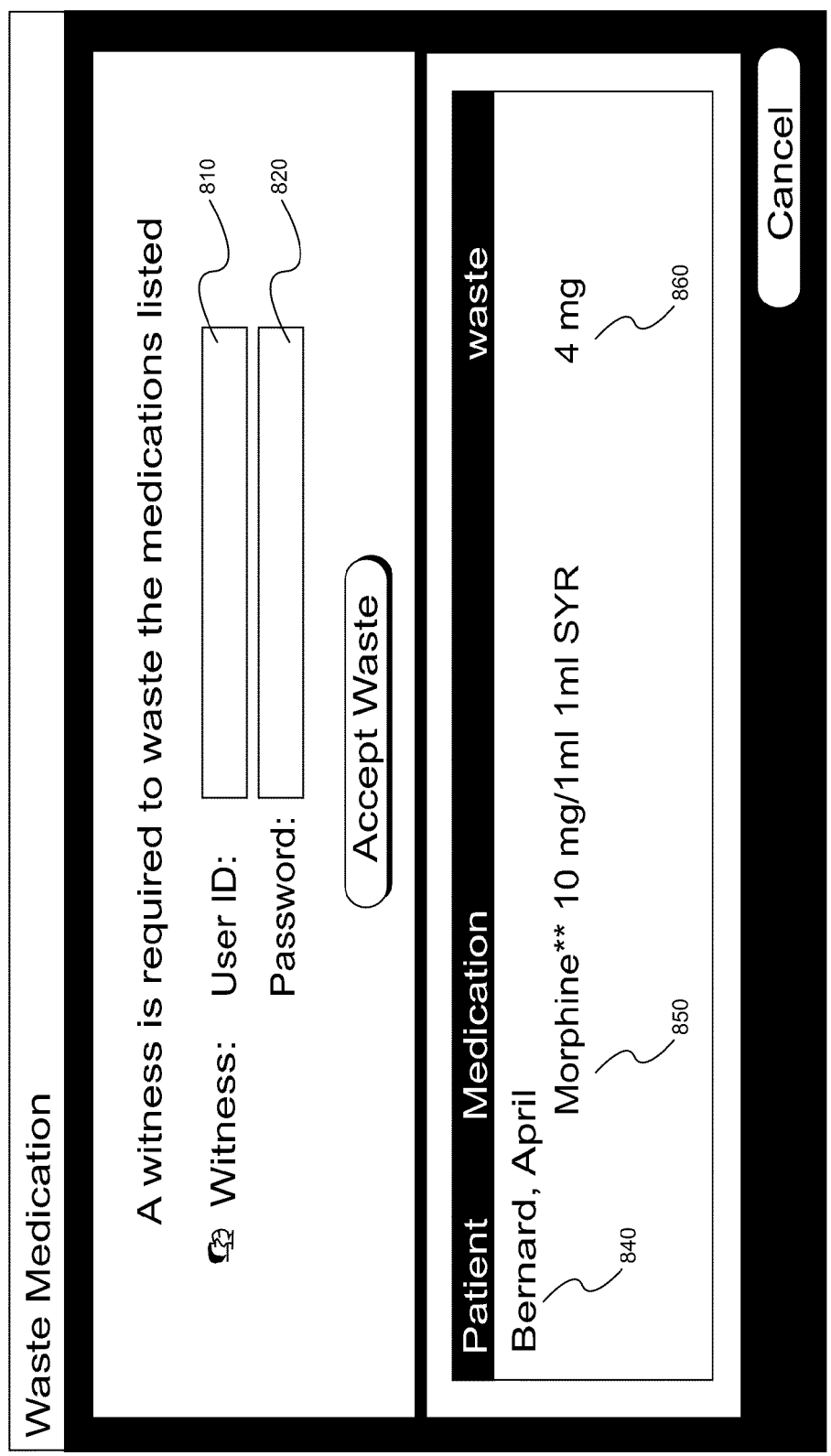
FIG. 8 illustrates an embodiment of a witness window.

FIG. 8 illustrates an embodiment of a witness window 800 that may appear when a user attempts to waste a medication or item that requires a witness. The display 800 may be associated with the waste and return screen 700 of FIG. 7, or it may be associated with some other waste or return system. A witness may be required to specify a user identification 810 and a password 820. The user may not be permitted to continue with the wasting process until the witness' login information has been validated at the remote terminal, the dispensing device or the central server computer system. Alternatively, the witness may only have to input her name. In some embodiments the patient's name 840 and amount 860 and name 850 of an item to be wasted is displayed. In some embodiments, the witness pop-up window may list more than one item or medicine requiring wasting. A check may be performed at the remote terminal, the central server computer system, or the dispensing device that the witness is a different person than the user. This prevents a user from acting as both the person wasting the item or medicine and the witness.

The ability to remotely enter and document a witness, such as in witness window 800, may be especially useful for both wasting and return of items. A person may have time to be a witness, but only if it takes a very short amount of time. For example, a fellow nurse may be willing to witness the wasting of an item and quickly document the wasting remotely at a remote device. However, that same nurse may not be willing to witness the wasting of an item if documenting the wasting requires a trip to a dispensing device that is inconveniently located.

Figure 9:
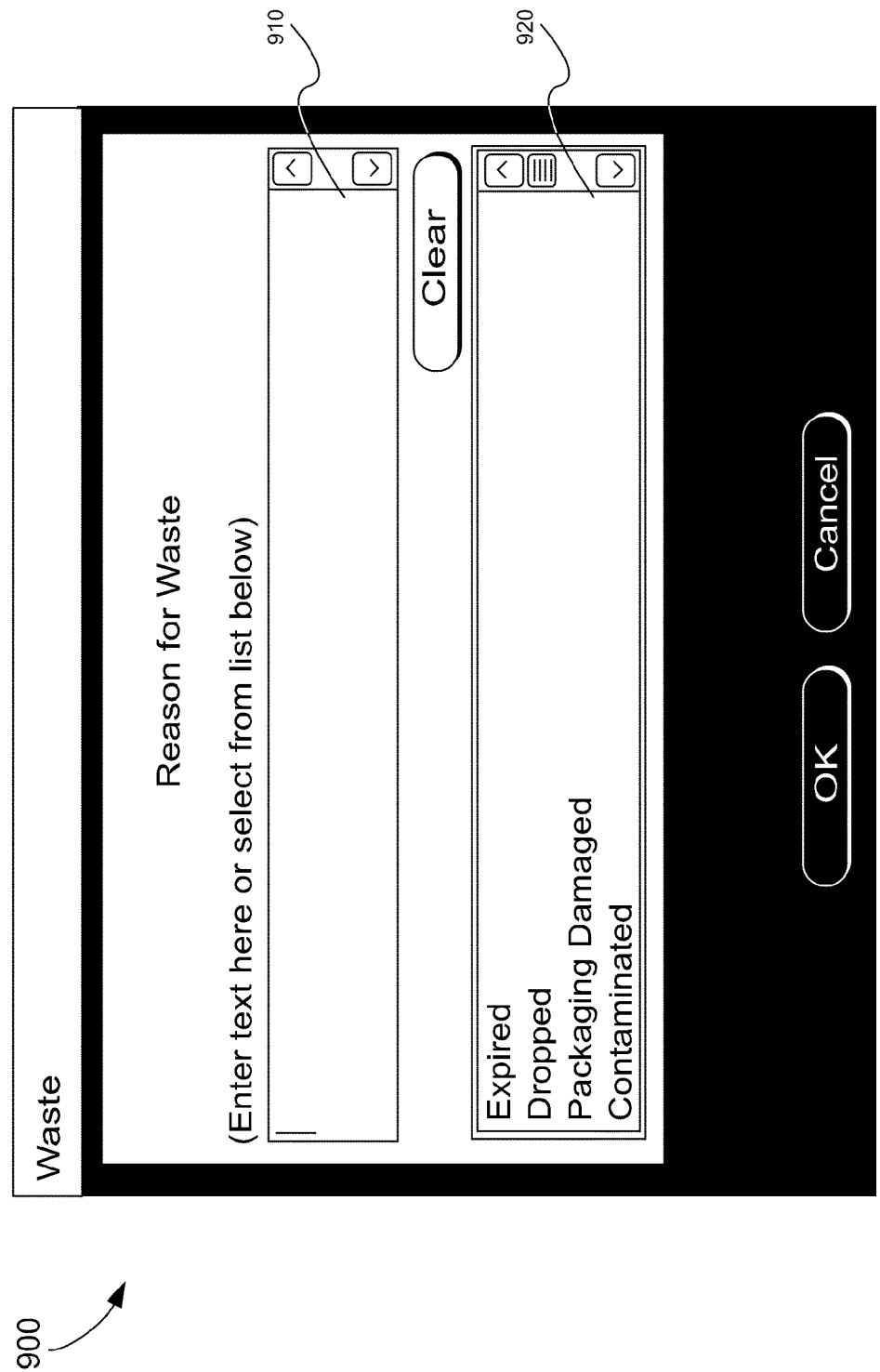
FIG. 9 illustrates an embodiment of a reason for waste window.

The user may be prompted with a question regarding the reason for the waste, such as in waste window 900 in FIG. 9. Such a window may display following, before, or instead of a witness window such as witness window 800 of FIG. 8. For example, particular items may require a reason for wasting. The reason for waste window 900 may always display, or may display only for those items or medicines which require a reason. The user may manually enter a reason 910 for the waste, or may selected a reason 920 from a list.

The ability to answer questions remotely from a dispensing device may be especially useful. Providing detailed, accurate answers at a dispensing device may be difficult if impatient users are waiting to use the dispensing device. Also, it may be easier to enter a detailed description from a remote device, such as a laptop or computer while sitting at a desk, as opposed to standing at a dispensing unit.

Figure 10:
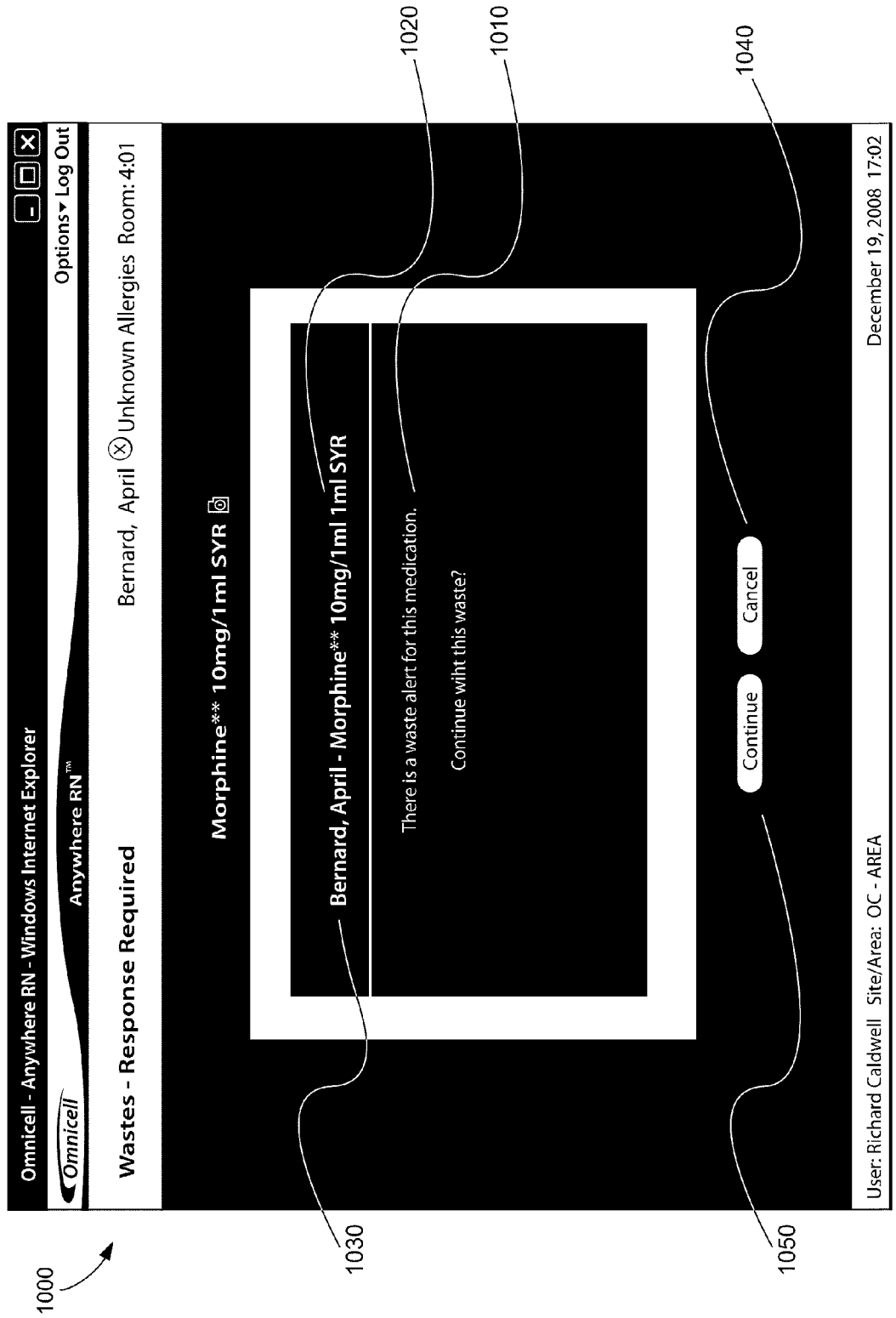
FIG. 10 illustrates an embodiment of a waste dispensing alert window.

Other alerts may be displayed during the wasting process. A waste dispensing alert window 1000 of FIG. 10 may be displayed after a witness window, such as 800 of FIG. 8, a reason for waste window 900 of FIG. 9, or a waste and returns window 700 of FIG. 7. A waste dispensing alert window 1000 may appear for each item or medicine being wasted. The waste dispensing alert window 1000 may display the patient's name 1030 and the item or medicine 1020 being wasted along with the amount. The user may be prompted to confirm the waste 1010. The user may be presented an option of whether to continue 1050 with the waste or cancel 1040.

Figure 11:
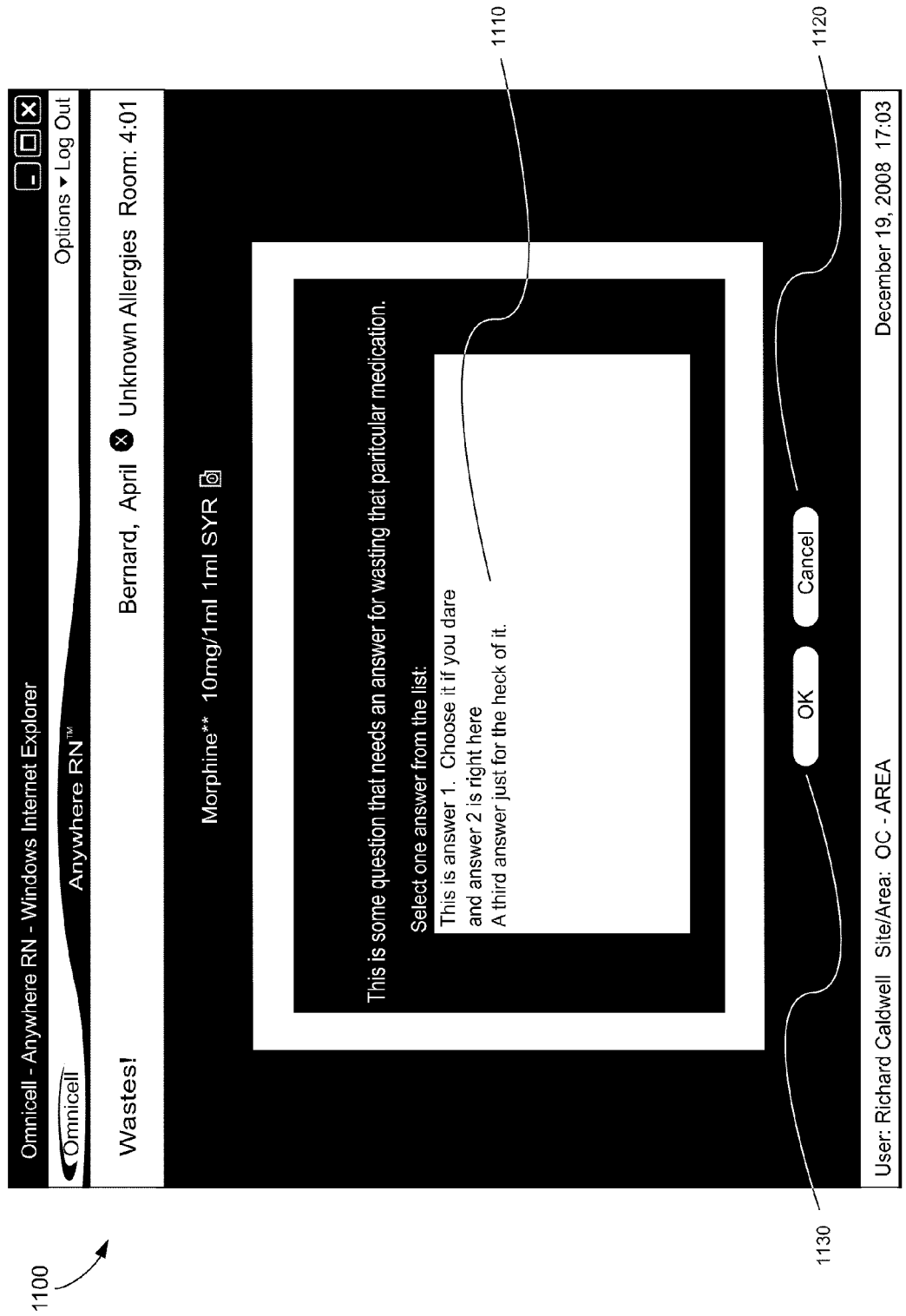
FIG. 11 illustrates another embodiment of a waste dispensing alert window with a question regarding the item.

FIG. 11 illustrates another waste dispensing alert 1100. This alert may be displayed following a selection of a user that requires a wasting of an item or medication. Some items or medications may require specific questions to be answered regarding the item or medication. The alert may pose a question, with the user choosing among a selection of answer choices 1110. There may be one or multiple questions for a particular item or medication. Again, the user may have the option of continuing by responding "ok" 1130 or canceling the wasting by responding "cancel" 1120.

Following the user completing all steps relating to confirmation, witnesses, and reasoning, the wasting process will be complete. In some embodiments, the remote terminal or the dispensing device the data was entered on by the user may be recorded. In some embodiments, the patient information displayed on the waste and returns window 700 of FIG. 7 will be updated with the completed wasting information.

In addition to wasting, the user may determine to return an item to the dispensing unit. For example, if an item is still viable to be used for another patient at a future time, the user may wish or be required to store the item or medication in the same dispensing device she initially removed it from, or in a different dispensing device. If the item was initially acquired from some other dispensing location, such as a central pharmacy, they item may still be eligible to be returned to a dispensing device or the dispensing location it was initially acquired from. While the physical item will need to physically be placed in or at a dispensing unit, the information accompanying the return may be provided to the center computer server system from a dispensing unit or a remote location.

Entering return information via a returns screen from a remote device may allow a user to at least partially complete the documentation of the return of an item or a portion of an item remotely. This may decrease the amount of time the user must spend inputting information to a dispensing unit. This may be especially useful if multiple users wish to use the dispensing unit or a large amount of information is required to document the return. For example, at a hospital, the user may wish to document the return from her desk, then drop off the item at a more convenient time. While the user may still need to physically visit the dispensing device, a minimum of information, such as only the user's username and password may need to be provided at the dispensing device.

Figure 12:
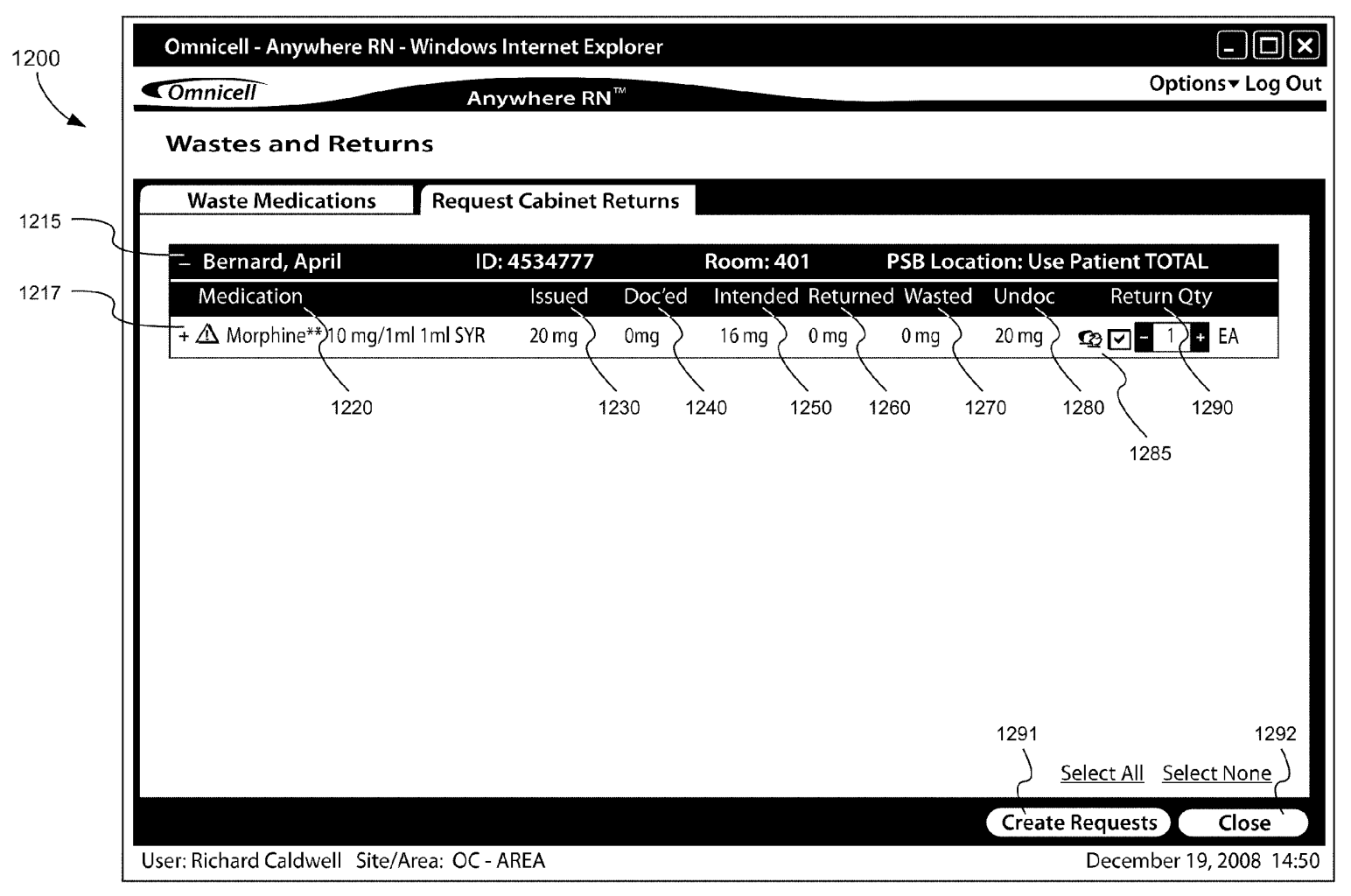

FIG. 12 illustrates an embodiment of a return window 1200, which may be used to remotely or locally stage a return transaction. The return window 1200 may function as a tab 1210 of a "Waste and Return" window as illustrated in FIG. 7, or may function as a separate stand-alone window. The return window 1200 may provide information 1215 such as a patient's name, a patient's identification number, and/or her room number. The return window 1200 may provide a listing of all medication associated with a patient or only those medications that are required to be returned. An item may only be displayed in the return window 1200 if sufficient quantity of the item is available for return. For example, the item may only be eligible for return if it is at least the package size of the item. If a certain medicine is available in 100 mg packets, the item may appear in the return window 1200 only if 100 mg are eligible to be returned. If 50 mg of the 100 mg has been used, the medicine may not appear in the return window 1200.

The return window may provide several categories of information regarding the patient and item or medicine to be returned, including categories entitled: Medication 1220, Issued 1230, Doc'ed 1240, Intended 1250, Returned 1260, Wasted 1270, Undoc 1280, and Return Qty 1290. Each of these categories of information may be information similar to those categories described in relation to the "Wastes and Returns" window of FIG. 7. As those with skill in the art will understand, information displayed may vary considerably depending on the industry or type of item being documented. The "Return Qty" 1290 may allow the user to specify the amount of an item to be returned. The "Return Qty" 1290 may be listed by package quantity. The "Return Qty" 1290 may be a plus/minus control, forcing the user to enter a whole package number of items to be returned. A witness may be required to execute a valid return. An icon 1285 may be used to identify that a witness is necessary for the return. The requirement of a witness may result in windows and prompts similar to those presented in FIG. 8. In some embodiments, because a return must physically be conducted at a dispensing unit, the witness may not provide identification information or confirmation information until the witness is present at the dispensing device. Despite the need for the witness to be physically present at the dispensing device, a significant time savings for the nurse may still occur. For example, if the nurse is aware ahead of time that a witness is required, he may be saved from traveling to the dispensing device, being prompted for witness information, and then setting out to search for a viable witness. Rather, the nurse may find a viable witness on his initial trip to the dispensing device.

An icon 1217 or other alert may be displayed if the patient 1215 has no active or future orders for a medication 1220. After entering a return quantity, the user may create the return request 1291 or cancel the return request by selecting close 1292. The list of items to be returned may be blocked from editing if information required to proceed has not been provided. The list may also be uneditable if the network connection of the remote device or dispensing device is not functioning properly.

After a request is created the return may be displayed or marked as "incomplete" or "pending" until the return is received by a dispensing device. Pending Returns window 1200*b* in FIG. 12*b* illustrates a possible embodiment of a pending returns window accessible by the user. A window 1200*b* may be accessible as a tab 1210*b* through another window or it may be a stand-alone window. The user may be able to adjust the quantity to be returned 1230*b*, or cancel a return 1240*b*. A dispensing device or location 1220*b* may be listed as where the item is due to be returned. After the item is received at the dispensing device, the return may be marked "completed," removed from the "Pending Returns" window 1210*b*, or otherwise denoted as returned to a dispensing device.

Figure 13:
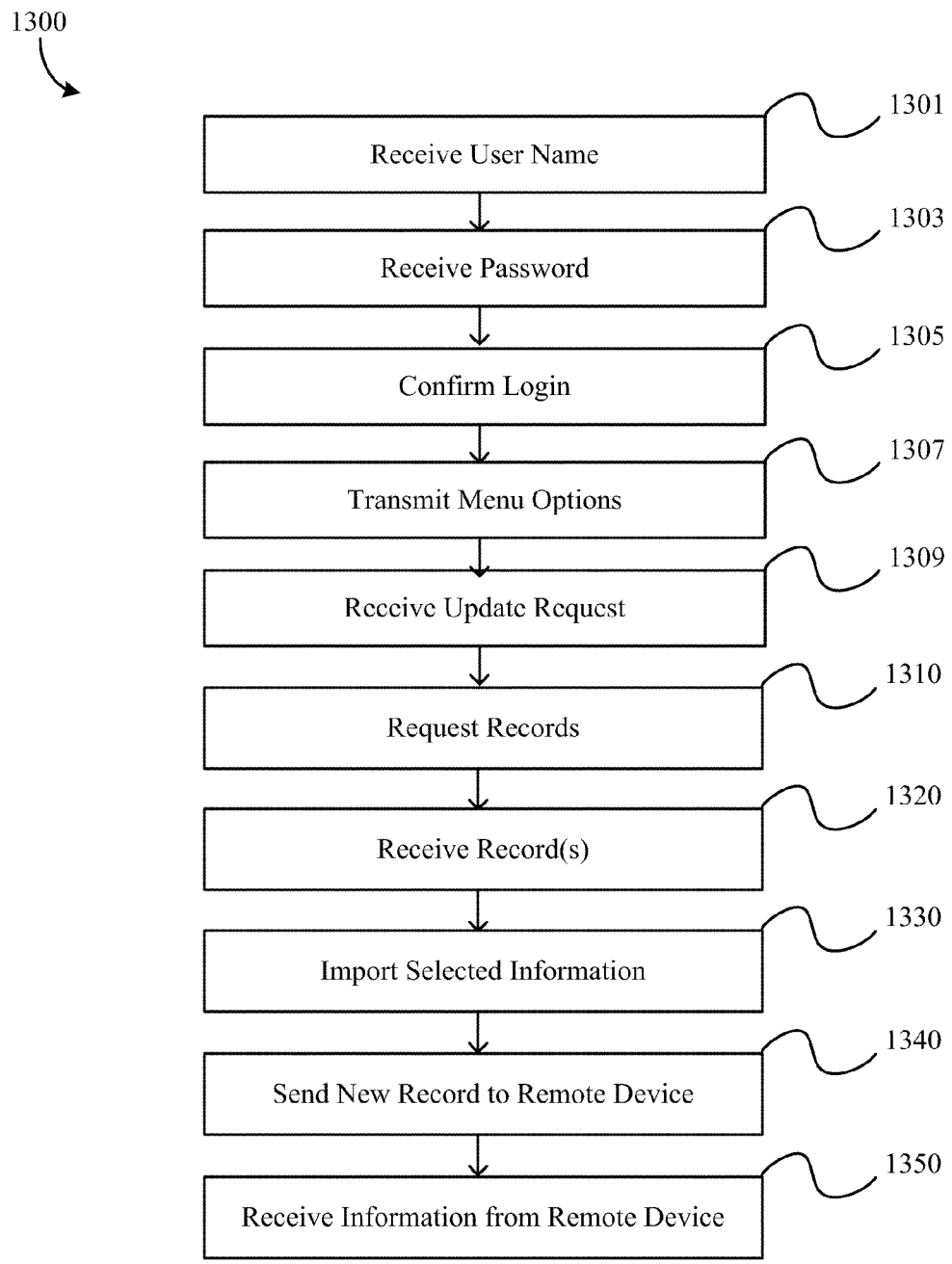
FIG. 13 illustrates an embodiment of a method of receiving patient record information.

FIG. 13 illustrates an embodiment of a method 1300 of receiving patient record information. Such a method may be used to import information to a central server computer system from an administration records computer server system, such as illustrated in FIG. 2. The central computer server system may receive a user name 1301 and a password 1303 from a remote terminal. The central computer server system may then confirm 1305 the user name and password. The confirmation 1305 may include determining whether the user has access to the central computer server system, to dispensing devices, and/or to specific dispensing devices in the user's vicinity. Once the user name and identity have been confirmed 1305, menu options may be transmitted to the terminal. The user may select and transmit to the central computer server system an update request 1309 for new or modified patient records. In some embodiments, the user may not need to request an update, with the new patients being automatically imported to the central computer server system.

Upon receipt of the update request 1309, the central computer server system may request records from the administration records computer server system. In some embodiments, the administration records computer server system may automatically send the central computer server system new or updated patient records whenever one becomes available or after a predefined period of time, such as every ten minutes. In some embodiments, the central computer server system is incorporated with the administration records computer server system, and no updates are necessary. Following the request for records 1310, the central computer server system receives the new or modified record or records 1320. The record may be imported 1330 as a whole, or selected parts of the record may be imported. For example, the patient's name, room number, and patient identification number may be imported, but his symptoms and eye color may not be. In some embodiments, all of the patient's information is imported.

Following the information being imported or incorporated into the record at the central computer server system, the new record may be transmitted 1340 to the remote device. The user may then view the record and modify it. Finally, the central computer server system may receive 1350 additional or modified information about the record from the remote device. Such information may relate to items or medication being administered to the patient. Portions of this method may repeat to update or modify the record on the central computer server system as new information becomes available to the user or the administration records computer server system.

Figure 14:
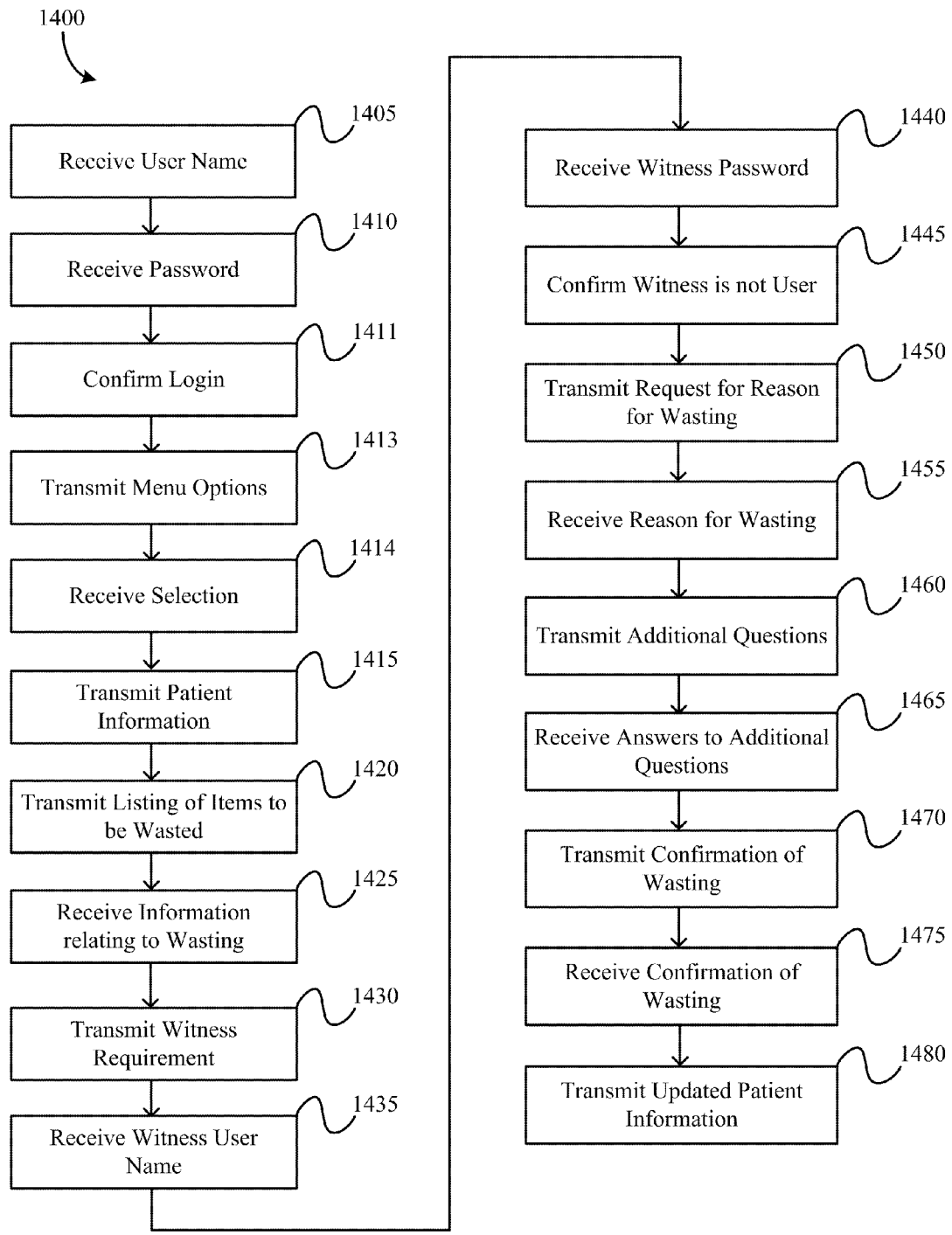
FIG. 14 illustrates an embodiment of a method of wasting an item or a portion of an item.

FIG. 14 illustrates an embodiment of a method 1400 of wasting a portion of an item removed from a dispensing device. First, the user may be required to log in. This may require transmitting from a remote device to the central computer server system the user name 1405 and/or password 1410 of the user. Alternatively or additionally, biometric information may be used to confirm the identity of the user. Once the user name and password are received by the central computer server system, the user's permission to access the central computer server system, dispensing devices, or dispensing devices in the user's vicinity is verified. Once it is confirmed the user has the right to access the central computer server system, menu options are transmitted 1413 to the remote terminal. Alternatively, the user's identity may be verified at the remote terminal, with no transmissions to the central computer server system.

The central computer server system may then receive 1414 a selection from a menu. The selection made by the user at the remote terminal may include specifying that an item is to be wasted. The central computer server system may transmit patient information 1415 to the remote device. This patient information may include a listing of items removed from a dispensing device for use with the patient, the dosing of the item, the patient's name, and the patient's room number. The patient information may be include all patients associated with the user or may be only patients associated with an item that requires wasting. The central computer server system may transmit 1420 a listing of items that are required to be wasted.

The central computer server system may then receive 1425 information related to wasting. This may include a quantity of an item to be wasted. In response to receiving this information on wasting, the central computer server system may transmit a witness requirement 1430. This witness requirement may be similar to witness window 800 of FIG. 8, or may be some different witness information. In response, the central computer server system may receive information, including the witness' user name 1435 and password 1440 from a witness at the remote terminal. The central computer server system 1445 may then confirm that the witness is a different person than the user.

In some embodiments, the central computer server system may transmit 1450 a request for a reason for wasting the item may be requested from the user or witness. The request for a reason for wasting the item may be in the form of a window, such as window 900 in FIG. 9, or in some other form. The central computer server system may then receive 1455 the reason for wasting. The central computer server system may then transmit 1460 an additional question or questions, and subsequently receive 1465 the answers to those questions.

Finally, a confirmation may be transmitted 1470 from the central computer server system to the remote device confirming the wasting. The confirmation may display in the form of a window, such as window 1000 in FIG. 10. The user may then proceed or cancel. If the user proceeds, the central computer server system receives 1475 confirmation of the wasting. Updated patient information may then be transmitted 1480 to the remote device.

Figure 15:
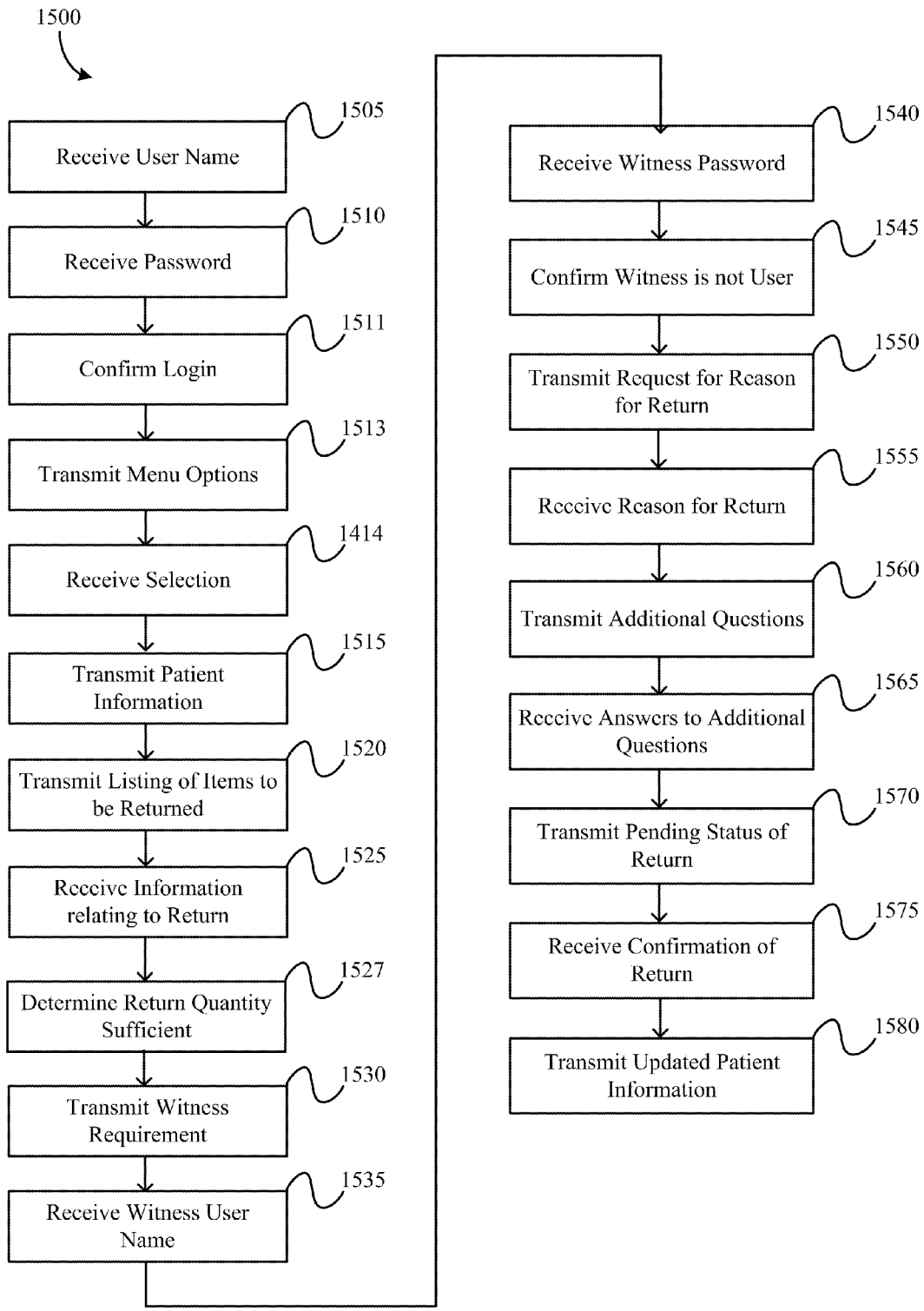
FIG. 15 illustrates an embodiment of a method of returning an item or a portion of an item to a dispensing device.

FIG. 15 illustrates an embodiment of a method 1400 of returning an item or a portion of an item previously removed from a dispensing device, or otherwise issued or checked out to a user. First, the user may be required to log in. This may require transmitting from a remote device to the central computer server system the user name 1505 and/or password 1510 of the user. Alternatively or additionally, biometric information may be used to confirm the identity of the user. Once the user name and password are received by the central computer server system, the user's permission to access the central computer server system, dispensing devices, or dispensing devices in the user's vicinity is verified. Once it is confirmed the user has the right to access the central computer server system, menu options are transmitted 1513 to the remote terminal. Alternatively, the user's identity may be verified at the remote terminal, with no transmissions to the central computer server system.

The central computer server system may then receive 1514 a selection from a menu. The selection made by the user at the remote terminal may include specifying that an item is to be wasted. The central computer server system may transmit patient information 1515 to the remote device. This patient information may include a listing of items removed from a dispensing device for use with the patient, the dosing of the item, the patient's name, and the patient's room number. The patient information may include all patients associated with the user or may only be patients associated with an item that requires wasting. The central computer server system may transmit 1520 a listing of items that are required to be returned or require that a portion of the item be returned.

The central computer server system may then receive 1525 information related to the return. This may include a quantity of an item to be returned. Based upon the information relating to the return, the central server computer system may determine 1527 whether the quantity is sufficient to be returned to a dispensing device. If not, the process may be halted, or the user may be instructed to waste the remainder of the item. In response to receiving this information on wasting, the central computer server system may transmit a witness requirement 1530. This witness requirement may be similar to witness window 800 of FIG. 8, or may require different witness information. In response, the central computer server system may receive information, including the witness' user name 1535 and password 1540 from a witness at the remote terminal. The central computer server system may then confirm 1545 that the witness is a different person than the user.

In some embodiments, the central computer server system may transmit 1550 a request for a reason for returning the item may be requested from the user or witness. The request for a reason for wasting the item may be in the form of a window, such as window 900 in FIG. 9, or in some other form. The central computer server system may then receive 1555 the reason for return. The central computer server system may then transmit 1560 an additional question or questions, and subsequently receive 1565 the answers to those questions.

A pending status may be transmitted 1570 from the central computer server system to the remote device confirming the return. The return may remain in a pending state until the return is received at a dispensing device. Transmitting 1570 a pending status may also include transmitting a message to a dispensing device or multiple dispensing devices that the user will be returning a item or a portion of an item. The central computer server system may then receive login information from a dispensing device. This may be to confirm the user's identity, or to associate a pending return stored at the central computer server system with the user. In some embodiments, verification of the user at the dispensing device, with no transmission to the central computer server system. Additional information may then be required to be entered at the dispensing device. The user may then return the item to the dispensing device. Once the item or portion of the item is received at a dispensing device, the central server computer system may receive 1575 a confirmation from the dispensing device. Updated patient information may then be transmitted 1580 to the remote device.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, structures, and techniques have been shown without unnecessary detail in order to avoid obscuring the embodiments.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "data stores", "central server computer system," and "administrative records computer server system" may represent one or more devices for storing data, including read-only memory (ROM), random access memory (RAM), magnetic RAM, core memory, magnetic disk storage mediums, optical storage mediums, flash memory devices, or other computer-readable mediums for storing information. The term "computer-readable medium" includes, but is not limited to, portable or fixed storage devices, optical storage devices, wireless channels, a sim card, other smart cards, and various other mediums capable of storing, containing, or carrying instructions or data.

Furthermore, embodiments may be implemented by hardware, software, firmware, middleware, microcode, hardware description languages, or any combination thereof. When implemented in software, firmware, middleware, or microcode, the program code or code segments to perform the necessary tasks may be stored in a computer-readable medium such as a storage medium. Processors may perform the necessary tasks.

What is claimed is:

1. A method for remotely managing items that are configured to be stored in at least one dispensing device, the method comprising:
    receiving user identification information at a host computer system from an electronic device that is remotely located from the dispensing device;
    transmitting from the host computer system to the electronic device a disposition of an item, wherein the item is associated with a patient; and
    receiving, at the host computer system from the remote electronic device, information about the item originating from the dispensing device, wherein:
        the information includes a further disposition of the item; and
        the further disposition of the item involves wasting at least a portion of the item or the item being returned to the dispensing device.

2. The method of claim 1, further comprising receiving at the host computer system from the electronic device patient identification information of the patient.

3. The method of claim 1, further comprising transmitting, to the remote electronic device from the host computer system, a listing of items the user has removed from the dispensing device that have not yet been administered to a patient, wasted, or returned to the dispensing device.

4. The method of claim 3, wherein the listing of items includes at least a portion of an item to be wasted or at least a portion of an item to be returned to the dispensing device.

5. The method of claim 1, wherein at least a portion of the items are controlled medical substances or medical supplies.

6. The method of claim 5, further comprising transmitting, from the host device to the dispensing device, at least a portion of the information received at the host device from the remote electronic device on at least the portion of the controlled medical substance or medical supply.

7. The method of claim 6, further comprising receiving a confirmation at the host computer system from the dispensing device that at least a portion of the controlled medical substance or medical supply has been returned.

8. The method of claim 1, wherein the dispensing device is secured with a lock, and further comprising unlocking the lock prior to returning the item.

9. The method of claim 1, wherein the remote electronic device comprises a graphical user interface, wherein at least a portion of user input is received through the graphical user interface.

10. The method of claim 9, wherein the graphical user interface comprises a web browser.

11. The method of claim 5, wherein the further disposition of the controlled medical substance or medical supply involves wasting at least a portion of the item.

12. The method of claim 11, further comprising transmitting to the remote electronic device from the host computer system, information regarding wasting of at least a portion of a controlled medical substance or medical supply.

13. The method of claim 11, further comprising receiving at the host computer system from the remote electronic device information regarding wasting at least a portion of the controlled medical substance or medical supply.

14. The method of claim 11, further comprising receiving at the host computer system from the remote electronic device a reason for the wasting of at least a portion of the controlled medical substance or medical supply.

15. The method of claim 11, receiving at the host computer system, from the remote electronic device, information about a witness present for wasting of at least a portion of the item.

16. The method of claim 15, wherein the witness identifying information comprising logon information of the witness.

17. The method of claim 15, further comprising:
comparing the information about the witness to information about the user; and
determining the witness is not the user.

18. The method of claim 1, wherein the host computer system and the dispensing device are the same device.

19. A system for dispensing items, the system comprising:
a first and second dispensing device configured to hold a plurality of items, each dispensing device including a processor that is configured to receive user input;
a host system that is configured to communicate with a processor on each dispensing device, the host computer system configured to:
receive from an electronic device that is remotely located from the first and second dispensing devices user identification information;
receive from the electronic device a user request for a disposition of an item originating from the first dispensing device, wherein the item is associated with a patient;
transmit to the remote electronic device information regarding the further disposition of the item, wherein:
the further disposition of the item involves wasting at least a portion of the item or the item being returned to the second dispensing device; and
receive information from the user of the further disposition of the item.

20. The system of claim 19, wherein the host system is further configured to:
receive from the electronic device patient identification information of a patient.

21. The system of claim 19 wherein the first dispensing device and the second dispensing device are secured.

22. The system of claim 21, wherein the plurality of items is a plurality of medical supplies and pharmaceuticals.

23. The system of claim 19, wherein the first dispensing device and the second dispensing device are the same dispensing device.

24. The system of claim 19, wherein the host system and the first dispensing device are integrated.

25. The system of claim 19, wherein the remote user system comprises a web browser, wherein at least a portion of user input is received in the web browser.

26. A method of monitoring a distribution of items, the method comprising:
receiving, at a host computer system, at least a subset of data contained in a first patient record from an administration records system;
creating, at the host computer system, a second patient record, wherein the second patient record contains fields for information regarding medication of a patient;
incorporating, at the host computer system, at least a portion of the subset of data contained in the first patient record into the second patient record;
transmitting, from the host computer system, at least a portion of the second patient record to an electronic device remotely located from the dispensing device;
receiving, at the host computer system, a modification of the second patient record or an addition to the second patient record, wherein:
the modification or addition include a disposition of a controlled medical substance or supply stored in the dispensing device; and
the disposition of the controlled medical substance or supply involves wasting at least a portion of the controlled medical substance or supply or the controlled medical substance or supply being returned to the dispensing device.

27. The method of claim 26, wherein the host computer system and the electronic administration records system are the same system.

28. The method of claim 26, wherein the host computer system and the dispensing device are integrated.

29. The method of claim 26, wherein the modification or addition to the second patient record includes information regarding returning at least a portion of a controlled medical substance or supply to the dispensing device.

30. A system for dispensing items, the system comprising:
at least one dispensing device configured to hold a plurality of items, the dispensing device including a processor that is configured to receive user input;
a cart, the cart including a cart-based electronic device and a plurality of drawers configured to store items associated with a plurality of patients; and
a host system, the host system configured to communicate with a processor on the dispensing device and to communicate with the cart-based electronic device, the host computer system configured to:

transmit, to the cart-based electronic device, a first set of configuration data for the plurality of patients;

transmit, to the cart-based electronic device, a second set of configuration data that determines an assignment of at least one drawer of the plurality of drawers to at least one patient of the plurality of patients; and receive, from the cart-based electronic device, disposition information that indicates disposition of an item stored in a drawer of the plurality of drawers, the disposition information involving wasting at least a portion of the item or the item being returned to the dispensing device.

* * * * *